US 9,075,907 B2

(12) United States Patent
Fujimoto

(10) Patent No.: US 9,075,907 B2
(45) Date of Patent: Jul. 7, 2015

(54) MEDICAL DIAGNOSIS ASSISTANCE SYSTEM, MEDICAL CARE ASSISTANCE DEVICE, AND MEDICAL CARE ASSISTANCE METHOD

(75) Inventor: Katsuhiko Fujimoto, Saitama (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1533 days.

(21) Appl. No.: 12/022,480

(22) Filed: Jan. 30, 2008

(65) Prior Publication Data
US 2008/0183069 A1    Jul. 31, 2008

(30) Foreign Application Priority Data
Jan. 30, 2007    (JP) .................. 2007-018860

(51) Int. Cl.
*A61B 5/055* (2006.01)
*G06F 19/00* (2011.01)
*G01T 1/16* (2006.01)
(Continued)

(52) U.S. Cl.
CPC ............ *G06F 19/3437* (2013.01); *A61B 5/0035* (2013.01); *A61B 5/0042* (2013.01); *A61B 6/501* (2013.01); *G01T 1/1603* (2013.01); *G01T 1/1642* (2013.01); *G06F 19/322* (2013.01); *G06F 19/345* (2013.01); *G06F 19/3487* (2013.01); *A61B 6/4258* (2013.01)

(58) Field of Classification Search
CPC ..... A61B 6/501; A61B 5/0035; A61B 5/0042
USPC ................. 600/407, 410, 411, 425, 427, 544
See application file for complete search history.

(56) References Cited

U.S. PATENT DOCUMENTS 6,210,655 B1 *  4/2001  Stein ........................... 424/9.34
6,321,105 B1    11/2001  Jenkins et al.
(Continued)

FOREIGN PATENT DOCUMENTS

DE    102 59 793 A1    7/2004
JP    9-66040          3/1997
(Continued)

OTHER PUBLICATIONS

Victor L. Villemagne, et al., "Imaginem Oblivionis: the prospects of neuroimaging for early detection of Alzheimer's disease", Journal of Clinical Neuroscience, vol. 12, No. 3, XP004863232, Apr. 1, 2005, pp. 221-230.
(Continued)

*Primary Examiner* — Rochelle Turchen
(74) *Attorney, Agent, or Firm* — Oblon, McClelland, Maier & Neustadt, L.L.P.

(57) ABSTRACT

A medical diagnosis assistance system comprising an image data storage part, a substance distribution information acquiring part, a display part; and a control part. The image data storage part is configured to store image data of a brain function image. The substance distribution information acquiring part is configured to detect the signal from within the brain of a subject and to acquire, based on the detected signal, substance distribution information indicating the distribution of the quantity of specified endogenous substances in each part of the brain. The control part is configured to control the display part to display the brain function image and the image information based on said acquired substance distribution information.

16 Claims, 11 Drawing Sheets

(51) Int. Cl.
*G01T 1/164* (2006.01)
*A61B 5/00* (2006.01)
*A61B 6/00* (2006.01)

(56) References Cited

U.S. PATENT DOCUMENTS

| | | | |
|---|---|---|---|
| 6,377,833 B1* | 4/2002 | Albert | 600/410 |
| 2002/0103429 A1* | 8/2002 | deCharms | 600/410 |
| 2004/0142902 A1* | 7/2004 | Struijker-Boudier | 514/53 |
| 2005/0004458 A1* | 1/2005 | Kanayama et al. | 600/437 |
| 2006/0100679 A1* | 5/2006 | DiMauro et al. | 607/94 |
| 2006/0117397 A1 | 6/2006 | Rutkowski et al. | |
| 2007/0031328 A1 | 2/2007 | Kung | |

FOREIGN PATENT DOCUMENTS

| | | |
|---|---|---|
| JP | 9-98961 | 4/1997 |
| JP | 9-113470 | 5/1997 |
| JP | 2002-511312 | 4/2002 |
| JP | 2002-172106 | 6/2002 |
| JP | 2002-360538 | 12/2002 |
| JP | 2006-204551 | 8/2006 |
| JP | 2008-505116 | 2/2008 |
| WO | WO 02/061457 A2 | 8/2002 |
| WO | WO 02/061457 A3 | 8/2002 |
| WO | WO 2006/009887 A2 | 1/2006 |
| WO | WO 2006/009887 A3 | 1/2006 |
| WO | WO 2006/014382 A1 | 2/2006 |

OTHER PUBLICATIONS

Bradford C. Dickerson, et al., "Neuroimaging Biomarkers for Clinical Trials of Disease-Modifying Therapies in Alzheimer's Disease", The Journal of the American Society for Experimental NeuroTherapeutics, XX, XX, vol. 2, No. 2, XP025343821, Apr. 1, 2005, pp. 348-360.

Jack L. Lancaster, et al., Automated Talairach Atlas Labels for Functional Brain Mapping, Human Brain Mapping, vol. 10, XP008078122, Jan. 1, 2000, pp. 120-131.

Markus Schwaiger, et al., "MR-PET: Combining Function, Anatomy, and More", Medical Solutions, Special Edition Molecular Imaging, Sep. 2005, pp. 25-30.

Office Action mailed Nov. 13, 2012, in Japanese Patent Application No. 2008-003229.

European Office Action issued Jul. 19, 2012 in Patent Application No. 08001639.7.

* cited by examiner

MEDICAL DIAGNOSIS ASSISTANCE SYSTEM, MEDICAL CARE ASSISTANCE DEVICE, AND MEDICAL CARE ASSISTANCE METHOD

BACKGROUND OF THE INVENTION

1. Field of the Invention

This invention relates to a medical diagnosis assistance system, a medical care assistance device, and a medical care assistance method. In particular, this invention relates to a medical diagnosis assistance system, a medical care assistance device, and a medical care assistance method that are used in the medical care of central nerve diseases.

2. Description of the Related Art

With recent acceleration of the aging of society, the number of patients who have central nerve diseases such as Alzheimer's disease, Parkinson's disease, and the like has been increasing. Throughout the world, effort is continuing toward determining a cause, an early diagnosis, and the establishment of a method for medically treating illnesses related to central nerves. However, because understanding of the brain is insufficient, one can say that the status of these is still at the early stages.

Image examination by modality has been used as a means of effective medical care for diagnosis and research on central nerve diseases, such as MRI (Magnetic Resonance Imaging) devices and nuclear medicine diagnostic devises. Such nuclear medicine diagnostic devises includes PET (Positron Emission Computed Tomography) and SPECT (Single Photon Emission Computed Tomography) in addition to others.

Modality—which highly differentiates soft parts, such as using MRI devices—is applied in observation for morphological atrophy of the brain. Modality, which is capable of creating functional images, such as using fMRI (functional MRI) or the nuclear medicine diagnostic devises is applied in observation for the active state of a brain.

Recently, there has been significant development in the field of molecular imaging. Molecular imaging is categorized into two techniques. The first technique is the creation of the image of a nanometer-level molecule using light or X-rays, which is literally "molecular imaging." Fluorescence microscopes and X-ray microscopes are examples of this technique. This technique is mainly used in laboratories because of the problems of energy invasion depth into a body to image and also of exposure to nuclear radiation.

Meanwhile, the second technique of molecular imaging is one that uses the collection of peculiar labeling agents (ligand) for specified molecules, cells, and tissue. This second technique is for imaging the presence and behavior of tiny amounts of molecules via the amplification of signals by adding contrast agents such as RI (radioisotopes) to ligand. An example of this technique is nuclear medical examination (which uses PET and SPECT) by administering RI labeling agent. MRI molecular imaging, which uses improved molecular peculiarity by adding ligand to nanoscale magnetic material such as SPIO (Super-Paramagnetic Iron Oxide), is also an example of this technique.

The second technique results in low resolution, but there is high expectation for using this technique in clinical studies, because it can create images on presence and function of molecules within a living body. Especially at present, technology such as PET-CT has attracted attention whereby high-resolution morphological images (CT image) are combined to improve the low-resolution of functional images (PET image) so that high-resolution morphology can be displayed overlapping with functional information.

While approaches using imaging are being developed, studies from the perspective of substances are showing progress. Central nerve disease is mainly caused by functional disturbance, or metabolic disorders due to the accumulation of waste that accompany aging. Now, approaches for finding ways of medical treatment and tracing the causes of central nerve disease by studying this waste are beginning to show progress.

One result that has been attracting attention recently is β-amyloid (beta amiyloid) (Aβ), which is regarded as one substance that causes Alzheimer's disease. β-amyloid is sometimes referred to as β-amyloid plaque, amyloid-β, or amyloid-β protein. Aβ is beginning to be known to precipitate as crystals in the brain, and to accelerate cognitive disorders while precipitating.

Therefore, Aβ is designated as a target molecule (detection target molecule) and contrast agents are added to ligands that specifically accumulates to this. As a result, the accumulation of Aβ in the brain in the early stage that is difficult to be detected morphologically, can be detected. Thus, diagnosis of Alzheimer's disease will be possible at an extremely early stage, and means for suppression of the progression of symptoms can be initiated at an early stage. Furthermore, the relationship between Parkison's disease and abnormal secretion of dopamine is well known as a common knowledge. These prior arts related to a material approach are disclosed in Japanese Unexamined Patent Application Publications 2001-352991, 2004-157124, 2004-261172, and 2003-199460.

At the same time, MIT (Minimally Invasive Treatment) is gaining attention in the field of medical treatment. Examples of this means include shockwave calculus fragmentation therapy, cyber knife, and IMRT (Intensity Modulated Radiation Therapy).

Shockwave calculus fragmentation therapy is a method of medical treatment whereby strong shockwaves such as ultrasonic waves are irradiated from outside the body to crush crystals inside the body (refer to Japanese Unexamined Patent Application Publication 2005-261599, for example). Cyber knife and IMRT enable the highly effective medical treatment of local cancer parts as well as exposure to nuclear radiation along the irradiation pathway to decrease, by irradiating nuclear radiation from a plurality of directions based on a three-dimensional treatment plan (refer to Japanese Unexamined Patent Application Publication 2002-267754, for example).

Meanwhile, a study has been advanced that attempts to solve the substance causing Alzheimer's disease Aβ by irradiating ultrasonic wave energy low enough to have little impact on central nerve tissue. Furthermore, studies of a drug delivery system that performs medical treatment by transporting medicine to the target parts of the brain have been advanced (refer to Japanese Unexamined Patent Application Publication 2000-504697, for example).

However, with the prior art, we have been unable to discover the specific relation of what kind of effect wastes and similar substances existing in the brain have on central nerve functions as well as body function. While the accumulation of substances is in progress, we have been unable to predict what kind of impact can be made on the central nerve and body functions in the future. Therefore, it has been difficult to diagnose nerve-related disease in an early stage and to predict the status of clinical conditions, with high precision.

In addition, when performing medical treatment for central nerve disease such as the above, substances such as Aβ are accumulated in a plurality of parts within the brain. In this case, it is preferable to optimize timing and the order of medical treatment by considering the quantity of accumulated substances in each part and the level of importance of the body or central nerve function corresponding to each part. However, it has been difficult to improve the safety and effectiveness of medical treatment for central nerve disease because the prior arts have been unable to discover the relationship between substances existing within the brain and the central nerve or body function corresponding to a brain part.

SUMMARY OF THE INVENTION

The present invention has been devised to solve problems such as the above, and aims to provide a medical diagnosis assistance system, a medical care assistance device, and a medical care assistance method that enables to grasp the relationship between substances existing within the brain and the central nerve or body function.

The present invention also aims to provide a medical diagnosis assistance system, a medical care assistance device, and a medical care assistance method that have the potential to improve the effectiveness and safety of medical treatment on central nerve disease as another purpose.

A first aspect of the present invention is a medical diagnosis assistance system, comprising: an image data storage part configured to store image data of a brain function image; a substance distribution information acquiring part configured to detect the signal from within the brain of a subject and to acquire, based on the detected signal, substance distribution information indicating the distribution of the quantity of specified endogenous substances in each part of the brain; a display part; and a control part configured to control said display part to display the brain function image and the image information based on said acquired substance distribution information.

A second aspect of the present invention is a medical care assistance device, comprising: a storage part configured to store substance distribution information indicating the distribution of the quantity of specified endogenous substances in each part of the brain of a subject and image data of a brain function image; a display part; and a control part configured to control said display part to display image information based on said substance distribution information and the brain function image based on said stored image data.

A third aspect of the present invention is a medical care assistance method, comprising: acquiring image data of a brain function image; acquiring substance distribution information indicating the distribution of the quantity of specified endogenous substances in each part of the brain of a subject; and displaying image information based on said acquired substance distribution information and brain function image based on said acquired image data.

According to the first to third aspects of the present invention, it is possible to cause a display part to display an image information based on substance distribution information indicating the distribution of the quantity of specified endogenous substances in the brain, and to display a brain function image. Thus, it is possible to discover the central nerve and body function based on the displayed brain function image, as well as discover the substance in the brain based on image information based on substance distribution information. Moreover, it is possible to discover the relationship between the central nerve and body function and the substances existing within a brain by comparing both images.

Furthermore, according to the first to third aspects of the present invention, with the capability of discovering the relationship between the central nerve and body function and substances existing within the brain, it will be possible to determine a treatment plan such as the timing and sequence of medical treatment by considering the accumulative quantity of substances in each part and the level of importance of the central nerve and body function corresponding to each part of the brain. Thus, it is possible to improve the effectiveness and safety of medical treatment for central nerve disease.

DETAILED DESCRIPTION OF THE PREFERRED EMBODIMENTS

The medical diagnosis assistance system, medical care assistance device, and medical care assistance method according to the present invention are intended to assist in the medical treatment and diagnosis of central nerve disease, including Alzheimer's disease and the like. For this purpose, a brain function image is displayed, and image information based on substance distribution information indicating the quantity of specified endogenous substances within the brain is displayed. They are displayed in parallel or with overlapped. Hereinafter, preferred embodiments according to the present invention will be described in detail with reference to drawings.

System Structure

Figure 1:
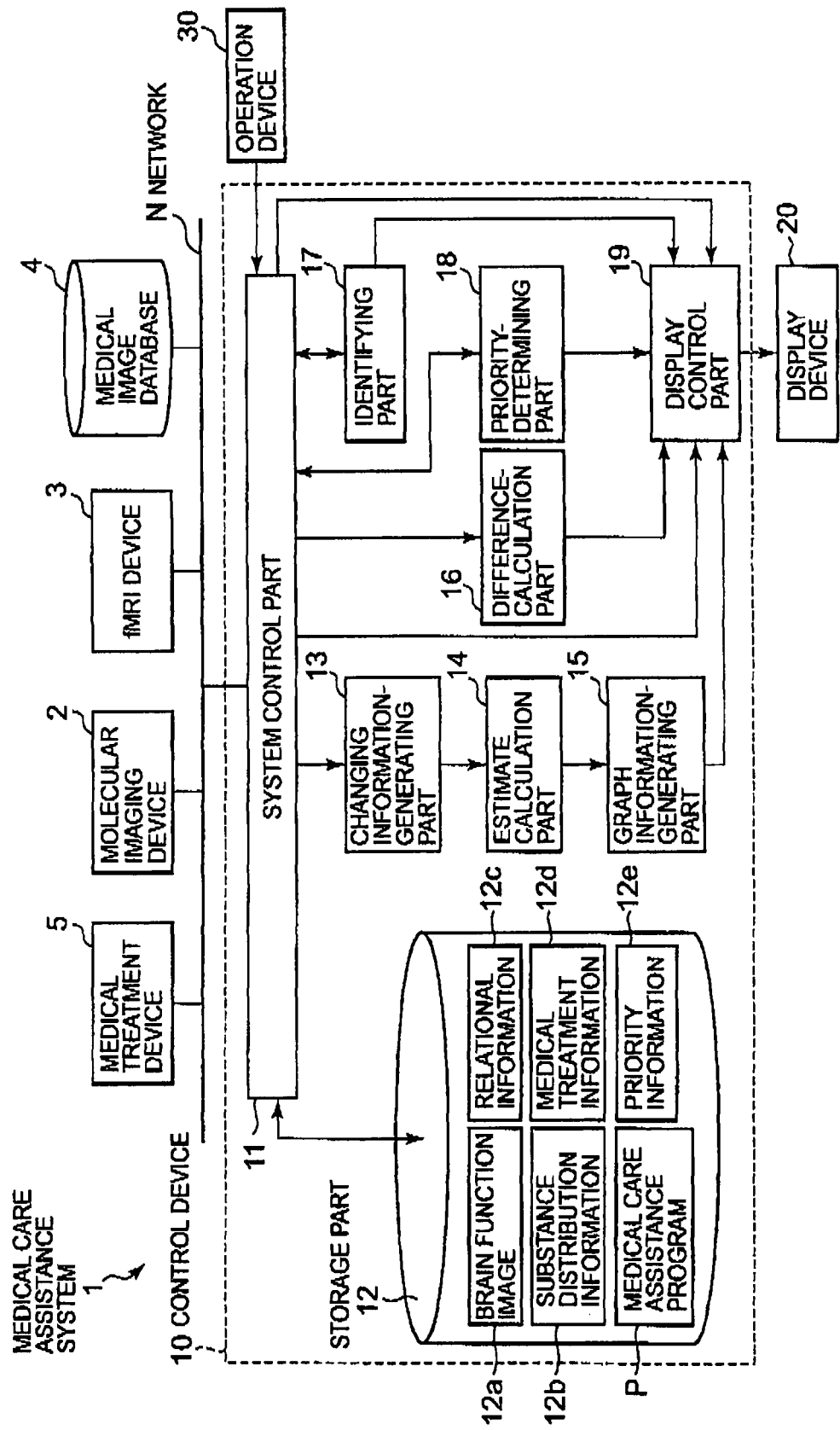
FIG. 1 is a schematic block diagram showing an example of embodiments of the overall structure of the medical diagnosis assistance system according to the present invention.

FIG. 1 shows an example of the overall structure of the medical diagnosis assistance system according to the present invention. The medical diagnosis assistance system 1 shown in this drawing comprises a control device 10 that is the center of this system, a molecular imaging device 2, an fMRI device 3, a medical image database 4, a medical treatment device 5, a display device 20, and an operation device 30.

The control device 10, molecular imaging device 2, fMRI device 3, medical image database 4, and medical treatment device 5 are connected via a network N such as a LAN (Local Area Network) capable of communication. In addition, each of the display device 20 and operation device 30 are connected to the control device 10. Hereinafter, the parts of the components will be described.

Molecular Imaging Device

The molecular imaging device 2 is a device that acquires information indicating the distribution of the quantity of specified endogenous substances (hereinafter referred to as "substance distribution information") in the brain of a subject (not shown). The substance distribution information is sent to the control device 10 and is stored in the storage part 12 (described later). Furthermore, the molecular imaging device 2 corresponds to one of the examples of the "substance distribution information acquiring part" according to the present invention.

The term "molecular imaging" here is explained by the "second method of molecular imaging" described in the background of the invention. The molecular imaging device 2 comprises examples of a nuclear medicine diagnosis device and MRI devices. Inspection methods with the molecular imaging device 2 includes: adding a contrast agent to ligands specifically accumulated to specified molecules, cells, and tissue (sometimes referred to as specified molecules and the like); administering them to a subject; and detecting amplified signals from within the brain via the contrast agent, so as to create an image of the existence and the behavior of specified molecules and the like.

In the case of using a nuclear medicine diagnosis device as a molecular imaging device 2, for example, it is possible to acquire substance distribution information by nuclear medical examination operated with the administration of an RI labeling agent.

In the case of using RMI devices as molecular imaging device 2, for example, there is also MRI molecular imaging examination that includes adding ligands to nanoscale magnetic material such as SPIO. In the case of detecting Aβ as a specified endogenous substance, for example, it is possible to use a substance known as "FSB," which is obtained by binding styrylbenzene that binds specifically to Aβ, to fluorine adaptive to nuclear magnetic resonance (e.g., refer to the Web site http://mycasty.jp/anotu/html/2005-03/03-14-45658.html). In the case of using RMI devices, the molecular imaging device 2 may be considered as combination of the molecular imaging device 2 and an fRMI device 3.

"Specified endogenous substances" to be examined by the molecular imaging device 2 are arbitrary substances generated inside a subject's body; in particular, these are substances that have adverse effects on the body. Examples of "specified endogenous substances" include: Aβ, which is a substance that causes Alzheimer's disease; dopamine, which is related to Parkinson's disease; and active oxygen, which is related to the cause and progression of brain functional disorder. Furthermore, "specified endogenous substances" include brain cells that relate to the cause and progression of brain functional disorder such as cells that have died by apoptosis. Hereinafter, the case in which Aβ is the specified endogenous substance will specifically be described in detail, and other cases will be described below in part of the modified example.

fRMI Devices

The fRMI device 3 is a device for generating image data showing the active state of specified parts in the brain of a subject (hereinafter referred to as a "brain function image"). The fRMI device 3, for example, generates an image data of a brain function image showing the active state within a brain based on the increase in MR signals (magnetic resonance signals) corresponding to the increase in oxyhemoglobin in active parts of a brain (so-called "BOLD (Blood Oxygenation Level Dependent) method"). The generated image data of brain function image is sent to the control device 10 and is stored in the storage part 12 (described later).

The fRMI device 3 is one of the examples of a "brain function image-generating part" according to the present invention. It is possible to use PET and the like as the brain function image-generating part. Furthermore, it is possible to apply optical topography that generate a brain function image by analyzing a reflected near-infrared light at the cerebral cortex. However, fRMI devices are regarded as more effective devices in terms of the resolution and are able to determine the active state of deeper parts of a brain. It is also possible to apply electroencephalography, magneto-encephalography, and the like at the same time for the sake of acquiring the temporal alteration of a brain function at the same time (multi-modality measurements).

Medical Image Database

The medical image database 4 comprises systems including HIS (Hospital Information System) and PACS (Picture Archiving and Communication System), or the database provided in the systems. The medical image database 4 is one example of "image data storing part". It should be noted that the medical image database 4 may be provided inside the control device 10.

The medical image database 4 includes: a storage device such as a large-capacity hard disk drive, and software for managing data of images and the like stored on the storage device. The medical image database 4 performs data management for each subject, for example, by making files on each subject, based on subject identification information such as subject ID.

The medical image database 4 may be a database for managing image data of medical image and the attendant information (e.g. DICOM attendant information), or it may be a database for managing an electronic medical chart including such information. At any rate, the database may be constructed to be capable of offering image data of medical image to the control device 10. "DICOM" is an acronym for communications standards for medical images of "Digital Imaging and Communications in Medicine."

Medical Treatment Device

The medical treatment device 5 may, for example, be a device for operating MIT, used as a medical treatment for eliminating and detoxifying specified endogenous substances within a brain by irradiating shockwaves such as ultrasonic waves, or energy waves such as nuclear radiation. Such medical treatment may be shockwave calculus fragmentation therapy, cyber knife, IMRT, and the like.

Furthermore, the medical treatment device 5 may be a device used in a drug delivery system for eliminating and detoxifying specified endogenous substances in a specified part by delivering medicine to the specified part within the brain.

If the specified endogenous substance is Aβ, the medical treatment device 5 may also be a device used for medical treatment that disintegrates Aβ by irradiating ultrasonic wave energy low enough to have little impact on central nerve tissue.

Display Device

The display device 20 comprises arbitrary display devices including a CRT (Cathode Ray Tube) display and an LCD (Liquid Crystal Display). The display device 20 displays various images and screens based on the control of the control device 10. Display device 20 is an example of the "displaying part" according to the present invention.

Operation Device

The operation device 30 comprises arbitrary input and control devices such as a control panel, joystick, trackball, keyboard, and/or a mouse. As a user operates the control device 30, the control device 30 sends operation signal corresponding to operation content to the control device 10. Then the control device 10 functions based on the control signal. The control device 30 is an example of the "operation part" according to the present invention.

Furthermore, the display device 20 and the control device 30 may be constructed integrally. Some examples include a touch panel display or a pen tablet.

Control Device

The control device 10 is a device having a central role in the control of the medical diagnosis assistance system 1, as well as performing various arithmetic processes. The control device 10 is an example of the "control part" according to the present invention. The control device 10, not shown in the figures, comprises a communication device (such as a network adapter), a hard disk drive, ROM, RAM, and a microprocessor including a CPU.

The control device 10 comprises a system control part 11, a storage part 12, a changing information generating part 13, an estimate calculation part 14, a graph information generating part 15, a difference calculating part 16, an identifying part 17, a priority determining part 18, and a display control part 19. Hereinafter, each part of these components will be described.

System Control Part

The system control part 11 operates whole control in medical diagnosis assistance system 1 with operating whole control in device 10. The system control part 11 comprises a microprocessor or the like. Hereinafter, specific operation of the system control 11 will be described occasionally.

Storage Part

The storage part 12 stores various types of data. The storage part 12 is an example of the "storage part" according to the present invention. The storage part 12 comprises a storage device such as a hard disk drive or the like. The storage part is placed in the control device 10 in this embodiment, but it is possible to place the storage part outside the control device 10. For example, a storage device on a network N may be used as the storage part.

The storage part 12 stores (the image data of) the brain function image 12a, substance distribution information 12b, relational information 12c, medical treatment information 12d, and priority information 12e with the medical care assistance program P.

The medical care assistance program P is a computer program for controlling the medical diagnosis assistance system 1, particularly and operation control of the control device 10. Each part of the control device 10 functions as a microprocessor executes the medical care assistance program P.

The image data 12a of the brain function image is an image data of image indicating the active state of a specified part within a brain as stated above. The image data 12a of the brain function image is generated by an fRMI device 3. The image data 12a of the brain function image is entered into the control device 10 by the fRMI device 3, and is stored in the storage part 12 via the system control part 11. Alternatively, the image data 12a of the brain function image stored in the medical image database 4 may be stored in the storage part 12 by reading via the system control part 11 from the medical image database 4.

The image data 12a of the brain function image may be image data of a tomographic image of a brain in one or more slice positions or may be a three-dimensional voxel data (volume data). If it is volume data, the control device 10 (system control part 11, for example) performs an MPR (Multi Planar Reconstruction) process for generating a tomographic image in arbitrary slice positions, as needed. The image data 12a of the brain function image is information including brightness information (RGB gradation information if it is color image) and coordinate information of each pixel(voxel).

The image data 12a of the brain function image is added to attendant information. The attendant information includes the subject identifying information (such as subject ID) for identifying the subject, test time and date information, including the generated time and date (such as year, month, day, and time) of an image, and slice position information including the coordinate-indicating slice position.

Substance distribution information 12b is information indicating the distribution of the quantity of specified endogenous substances such as Aβ within a brain as mentioned above. The substance distribution information 12b is generated by a molecular imaging device 2. The substance distribution information 12b is entered into the control device 10 by the molecular imaging device 2, and is then stored in the storage part 12 via the system control part 11. Alternatively, the substance distribution information 12b stored in the medical image database 4 may be read by the system control part 11 and stored in the storage part 12.

The substance distribution information 12b is image data indicating the distribution of the quantity of specified endogenous substances such as Aβ within a brain. The substance distribution information 12b includes coordinate information of each pixel, and brightness information (RGB gradation information if it is color image) corresponding to the quantity of specified endogenous substances. The substance distribution information 12b may, for example, be image data of a tomographic image indicating two-dimensional distribution of the quantity of specified endogenous substances in a sliced position of a brain, or image data of a image indicating the three-dimensional distribution of the quantity of specified endogenous substances in a brain in whole or in part (volume data or image data of pseudo three-dimensional image acquired by rendering volume data).

Furthermore, the substance distribution information 12b may be information (e g., table information) relating the location information (coordinate information) of a part within the brain to the quantity of specified endogenous substances in that part.

The substance distribution information 12b is added to the attendant information, including the slice position information, test time and date information, and the subject identifying information similar to the image data 12a of the brain function image.

Relational information 12c is information that relates a brain part to part of the body or function controlled by the brain part. For example, "a part corresponding to hand movement in the motor cortex" as a brain part is related to a hand as a body part. Furthermore, "visual association cortex" as a brain part is related to the "visual perception" as a body function. Relational information 12c includes the relation information related to a plurality of brain parts and a plurality of body parts or functions. Relational information 12c is stored in the storage part 12 in advance (e.g., it is stored prior to actually operating the medical diagnosis assistance system 1).

Medical treatment information 12d includes information related to therapeutic regimen of a body part and the functional disorder for each part and function indicated in the relational information 12c. The medical treatment information 12d, for example, stores therapeutic regimen related to medical treatment, including rehabilitation that accelerates an alternative function of a brain (whereby a body part or a function is controlled by a brain part except the other brain part that is supposed to control it). The medical treatment information 12d is stored in the storage part 12 in advance.

Priority information 12e is information that associates a brain part with priority based on a body part or a function controlled by the brain part. This priority may, for example, be determined in advance according to importance of a body part or a function. One example of this priority ranks "visual performance" as a first, ranks "language function" as a second, ranks "hand (dominant hand in particular)" as a third, . . . . This priority information is stored in the storage part 12 in advance.

Changing Information-Generating Part

A changing information-generating part 13 generates information indicating the change in quantity over time of specified endogenous substances, based on a set of substance distribution information 12b acquired at a plurality of different dates and times via a molecular imaging device 2 (referred to as "changing information"). The changing information-generating part 13 is an example of the "changing information generating part" according to the present invention. The changing information-generating part 13 comprises a microprocessor or the like.

The process of generating changing information will be described specifically. Substance distribution information 12b, as mentioned above, is image data (or table information) indicating the distribution of the quantity of specified endogenous substances in a brain. In medical care of central nerve diseases, it operates a test on the quantity of specified endogenous substances on a regular basis such as on a yearly basis, or on a monthly basis for recognizing the effect of medical treatment and any change in clinical conditions. The substance distribution information 12b acquired from each test is added to the subject-identifying information and test time and date information, and is then stored in the medical image database 4 (or storage device such as a storage part 12).

The changing information-generating part 13 generates changing information based on a plurality of substance distribution information 12b (different test time and date) stored regarding the subject. Provided that the substance distribution information 12b is image data, the substance distribution information 12b would be information that includes coordinate information of each pixel and brightness information (or RBG gradation level; hereinafter, the same) corresponding to the quantity of specified endogenous substances. For a set of substance distribution information 12b, the changing information-generating part 13 acquires a plurality of information of the quantity of specified endogenous substances in each pixel, with reference to brightness information corresponding to the same coordinates (pixel) (—brightness information corresponding to the same part within a brain). As described above, the value of the brightness corresponds to an amount of existence. The plurality of information is information acquired from a plurality of times of test—information over time indicating the change in quantity over time of specified endogenous substances within a brain. As described, changing information is information that indicates the change in quantity over time of a specified endogenous substance in each brain part (coordinates). However, provided that image positions of the plurality of substance distribution information 12b are misaligned, it first aligns the plurality of the image positions by aligning feature points on the images, for example.

As substance distribution information 12b is table information, substance distribution information 12b is information relating the position information (coordinate information) of the brain part to the quantity of specified endogenous substances in that part. For each part within a brain, the changing information-generating part 13 generates information indicating the change in quantity over time of specified endogenous substances in a part, by extracting abundance information from a set of substance distribution information 12b.

Estimate Calculation Part

An estimate calculation part 14 calculates the estimate of the quantity of specified endogenous substances within a brain based on the changing information generated by the changing information-generating part 13. The estimate calculation part 14 is an example of the "estimate calculation part" according to the present invention and comprises a microprocessor or the like.

In the storage part 12, information regarding the estimate of change in substance quantity is stored in advance. Information regarding the estimate of change in substance quantity is information indicating the typical changing state of abundance of a specified endogenous substance. Information regarding the estimate of change in substance quantity may, for example, be generated from clinical data. Information regarding the estimate of change in substance quantity may, for example, be stored in conjunction with the medical treatment information 12d.

The information regarding the estimate of change in substance quantity may, for example, include information regarding estimate when not providing medical treatment and/or information of estimate when performing medical treatment. Information of estimate for performing medical treatment is information indicating the changing state of quantity of specified endogenous substances in the case of applying therapeutic regimen (including rehabilitation) indicated in the medical treatment information 12d. Information of estimate for not providing medical treatment is information indicating the changing state in the case of not applying the therapeutic regimen indicated in the medical treatment information 12d.

Information regarding the estimate of change in the substance quantity may be generated for every condition of a subject such as the age and gender. Furthermore, the information regarding the estimate of change in the substance quantity may be generated for every part within a brain in which specified endogenous substances exist.

An estimate calculation part 14 calculates the estimate of the quantity of specified endogenous substances with reference to the typical changing state of quantity indicated in the information regarding the estimate of change in substance quantity based on the quantity of specified endogenous substances indicated in changing information, information regarding brain parts, and the condition of the subject. The estimate indicates a future change in the specified endogenous substances in a brain part. The estimate calculation part 14 calculates a plurality of estimates such as on a monthly basis or a yearly basis.

Graph Information-generating Part

A graph information-generating part 15 generates graph information indicating the change in quantity over time of specified endogenous substances in specified parts within a brain based on changing information and the estimate calculated by the estimate calculation part 14. The graph information may, for example, be acquired by plotting a graph. On this graph, time is assigned to the horizontal axis, and the quantity of specified endogenous substances assigned to the vertical axis (described later). Further, the graph describes quantities of specified endogenous substances at a past time and date of examination indicated by the changing information, and the quantity of specified endogenous substances at a future time and date indicated by estimate. The graph information may, for example, be generated as image data. The graph information-generating part 15 comprises a microprocessor or the like.

Difference Calculation Part

A difference calculation part 16 calculates the difference between two sets of substance distribution information 12b acquired by the molecular imaging device 2 at a given internal. The difference calculation part 16 is an example of the "difference calculation part" according to the present invention and comprises a microprocessor or the like.

An example of the operation process as a difference calculation part 16 will be described. The storage part 12 stores a set of substance distribution information 12b acquired at different test times and dates. If each substance distribution information 12b is an image data, the difference calculation part 16 determines an image data of the difference image between the two substance distribution information 12b. The difference image is an image indicating the change in abundance distribution of specified endogenous substances at intervals of acquisition (corresponding to the "at a given internal" mentioned above) of the two substance distribution information 12b. This difference image is referred to as "an image of substance quantity changes".

If each substance distribution information 12b is table information, the difference calculation part 16 calculates, for each brain part (each coordinate), the difference between the two quantities of specified endogenous substances indicated in the two substance distribution information 12b. As each substance distribution information 12b is table information, the image data may be generated based on the relationship between the location information (coordinate information) of a brain part and the quantity of a specified endogenous substance, for each of the two substance distribution information 12b. Furthermore, a difference image (image of substance quantity changes) of the two images may be generated.

Identifying Part

An identifying part 17 identifies a body part or a function that has the possibility of incurring a functional disorder based on relational information 12c, substance distribution information 12b, and the image data 12a of the brain function image. The identifying part 17 is an example of the "functional disorder-identifying part" according to the present invention and comprises a microprocessor or the like.

An example of an operation process of the identifying part 17 will be described. Relational information 12c, as described above, is information relating a brain part to a body part or to a function controlled by the brain part. In addition, coordinates (pixel) of an image data 12a of the brain function image and coordinates of the substance distribution information 12b correspond to each other. If these coordinates do not correspond to each other, they are repositioned using image-positioning technology.

The identifying part 17 estimates the quantity of existing specified endogenous substance in each part (coordinate) of a brain based on substance distribution information 12b and brain function image 12a. Furthermore, the identifying part 17 relates each part of a brain to each part of a body or to a function with reference to relational information 12c. Thus, a body part or a function is related to the quantity of specified endogenous substances in a brain part corresponding the part or the function.

Furthermore, the identifying part 17 identifies the body part or the function corresponding to the brain part having a large quantity of specified endogenous substances. Accordingly, a body part or a function that has a possibility of incurring a functional disorder is identified. Therefore, the identifying part 17 may, for example, identify a body part or the like corresponding to the part where the quantity of specified endogenous substances is higher than a specified quantity. The identifying part 17 may also identify a body part or a function that has the possibility of developing a functional disorder by ranking from the highest quantity of specified endogenous substances. The identifying part 17 may also identify a body part or a function that has the possibility of developing a functional disorder by weighting based on the possibility of developing a disorder acquired clinically in each brain part (each body part or function).

Priority Determining Part

A priority determining part 18 determines the priority for performing medical treatment via a medical treatment device 5 for a plurality of brain parts based on a brain function image data 12a, priority information 12e, and substance distribution information 12b. The priority determining part 18 is an example of the "priority determining part" according to the present invention and comprises a microprocessor or the like.

An example of the operation process of the priority determining part 18 will be described. Priority information 12e is information that relates a brain part to a priority based on a body part or a function controlled by the brain part. The priority determining part 18 estimates the quantity of specified endogenous substances in each brain part (coordinate) based on substance distribution information 12b and the image data 12a of the brain function image. Furthermore, the priority determining part 18 relates a priority to each part having specified endogenous substances, with reference to priority information 12e. Thus, the medical treatment priority is determined corresponding to (a plurality of) a part having specified endogenous substances.

At this moment, the priority determining part 18 may determine the priority considering the quantity of specified endogenous substances in each part. In this case, the priority information 12e is regarded as information associating the priority with brain parts as well as the quantity of specified endogenous substances. For example, regarding "visual function" and "language function," assume that the quantity of a specified endogenous substance in a part within a brain associated with the "language function" is more than twice as much as the quantity in a part associated with the "visual function." In this case, the priority information 12e associates the "language function" with the first priority while associating the "visual function" with the second priority. In any other cases, the "visual function" is associated with the first priority while the "language function" is regarded as information to be associated with the second priority.

Display Control Part

The display control part 19 controls the display device 20 to display various types of images or screens. For example, the display control part 19 causes it to display two images overlapping or two images in parallel, based on two image data. At this moment, images based on the two image data may also be displayed separately, and image data in which two image data are combined (image data of a fusion image)

may be generated to display the fusion image. The display control part 19 is constituted to include a microprocessor or the like.

Operation

The operations of the medical diagnosis assistance system 1 comprising such a constitution are described below. Hereafter, four operations of the medical diagnosis assistance system 1 will be described.

The first operation describes an operation of the medical diagnosis assistance system 1 for displaying a brain function image and an image representing the distribution of a quantity of specified endogenous substances within a brain (referred to as a "substance distribution image").

The second operation describes an operation of the medical diagnosis assistance system 1 for displaying a brain function image and an image representing the changes of the distribution of a quantity of specified endogenous substances in a prescribed period (referred to as an "image of substance quantity changes").

The third operation describes an operation of the medical diagnosis assistance system 1 for displaying a body part or a function that has the possibility of developing a functional disorder.

The fourth operation describes an operation of the medical diagnosis assistance system 1 for displaying the priority when performing medical treatment with respect to a plurality of parts within a brain using the medical treatment device 5.

First Operation

Figure 2:
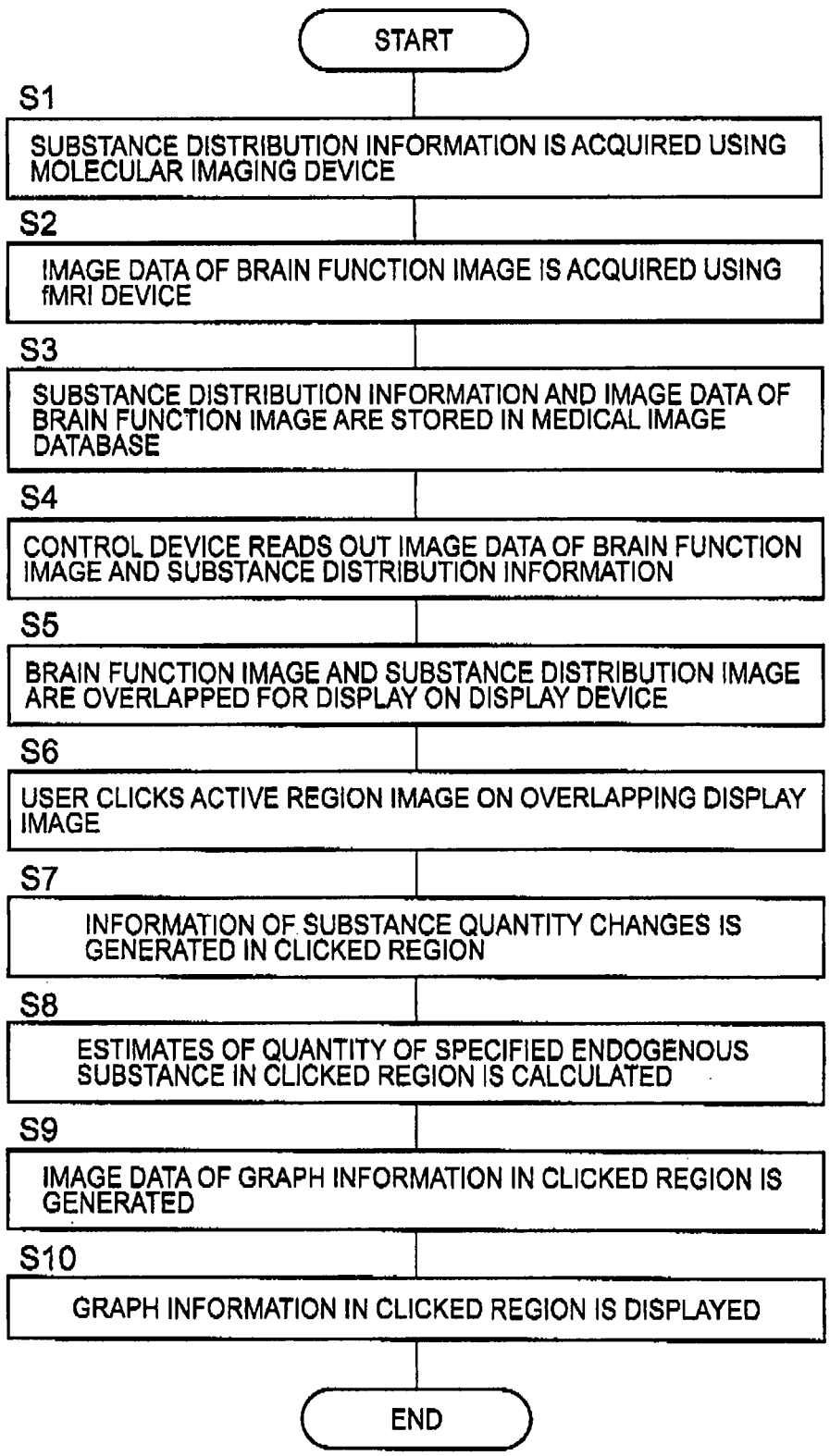
FIG. 2 is a flow chart showing an example of embodiments of operation of the medical diagnosis assistance system according to the present invention.

The flow chart shown in FIG. 2 represents one example of operations performed by the medical diagnosis assistance system 1 when a brain function image and a substance distribution image are displayed in the display device 20.

First, substance distribution information indicating the distribution of a quantity of specified endogenous substances within the brain of a subject is acquired using a molecular imaging device 2 (S1). Furthermore, image data of a brain function image representing the active state of a specified part within the brain of the subject is acquired using a fMRI device 3 (S2). Moreover, either the acquisition of the substance distribution information or the acquisition of the image data of the brain function image may be prioritized to be carried out.

The acquired substance distribution information and the image data of the brain function image are respectively sent to the medical image database 4 to be stored (S3). Herein, the medical image database 4 refers to the attendant information that has been attached to the substance distribution information as well as the image data of the brain function image, and stores the substance distribution information and the image data of the brain function image in a file related to the subject (patient).

The system control part 11 of the control device 10, for example, reads out image data 12a of a brain function image and substance distribution information 12b from the medical image database 4 in response to the request from a user and causes the storage part 12 to store the same (S4). Then, a plurality of the image data 12a of brain function images and the substance distribution information 12b on a plurality of examination dates/time are presumed to be read out.

An example of the process of Step S4 is specifically described. For example, when a user enters patient identification information by operating an operation device, the system control part 11 sends the patient identification information and a data transfer request to the medical image database 4. The medical image database 4 identifies the file that corresponds to the patient identification information and sends the image data 12a of brain function images and the substance distribution information 12b to the control device 10. The system control part 11 causes the storage part 12 to store the image data 12a of the brain function images and the substance distribution information 12b.

Furthermore, as for reading out the data from the medical image database 4, it is not necessary to read out all data at this stage. For example, it is possible to constitute with the following process so that necessary data is read out consecutively at an appropriate timing.

Then, once the image data 12a of the brain function images and the substance distribution information 12b are stored in the storage part 12, the system control part 11, for example, selects the image data 12a of brain function images and the substance distribution information 12b on the same examination date/time in response to an operation by the user. At this time, if the substance distribution information 12b is table information, the system control part 11 generates image data from the table information. The system control part 11 sends the selected image data 12a of brain function images and the substance distribution information 12b (image data) to the display control part 19. The display control part 19 causes the display device 20 to display the brain function image and the substance distribution image overlapping based on these two image data 12a and 12b (S5).

FIG. 3 shows one example of an image (overlapping displayed image) in which a brain function image and a substance distribution image have been overlapped. The overlapping displayed image is displayed in an image display region 110 of a specified screen for medical treatment 100.

Figure 3A:
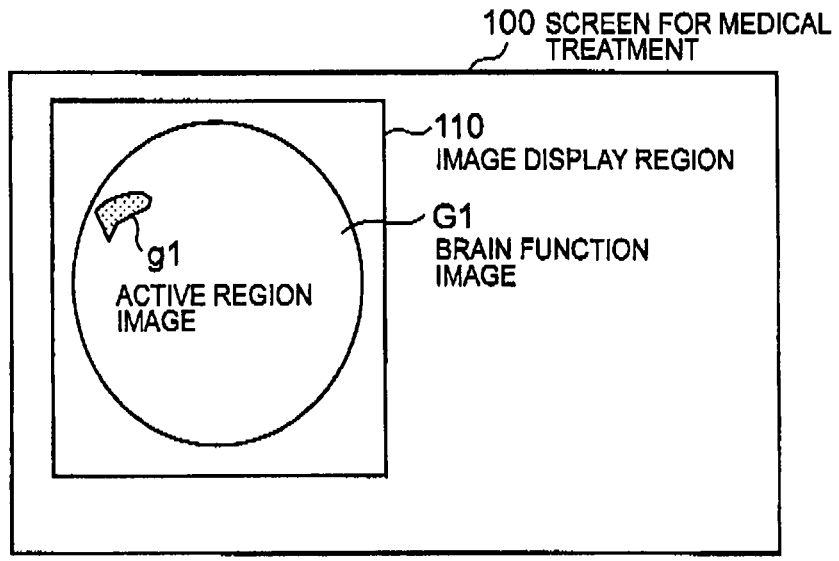
FIG. 3 is a schematic diagram showing an example of embodiments of image display of the medical diagnosis assistance system according to the present invention.

The brain function image G1 shown in FIG. 3(A) represents one example of images to be displayed based on the image data 12a of brain function images. The brain function image G1 is an image in which an active region image g1 is clearly shown on a tomographic image at a specified cross-sectional position of the brain. The active region image g1 represents a part within a brain that corresponds to the right hand of a body.

Figure 3B:
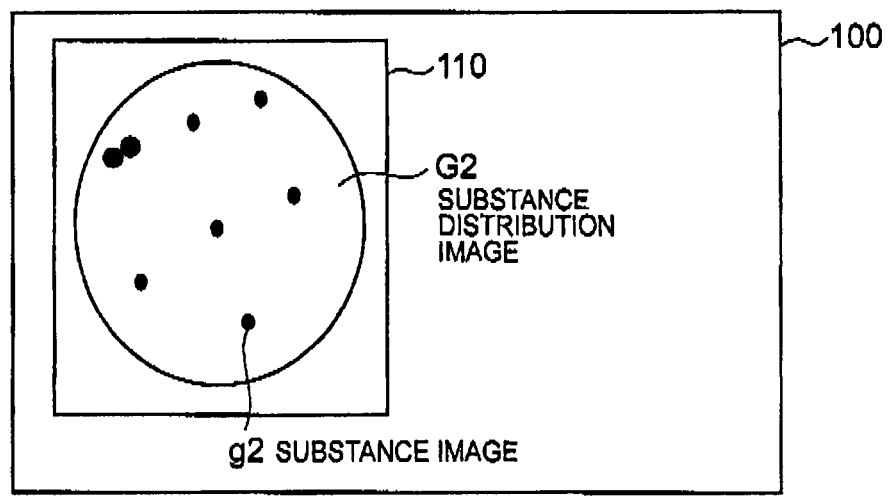

The substance distribution image G2 shown in FIG. 3(B) represents one example of images to be displayed based on the substance distribution information 12b. The substance distribution image G2 is an image in which a substance image g2 has been distributed on the same cross-sectional position of the brain as the brain function image G1. The substance image g2 represents the presence of a specified endogenous substance (Aβ). Moreover, at the cross-sectional position of the substance distribution image G2, the same tomographic image as the brain function image G1 may be displayed, and also simply an image showing the cross-sectional position may be displayed.

Figure 3C:
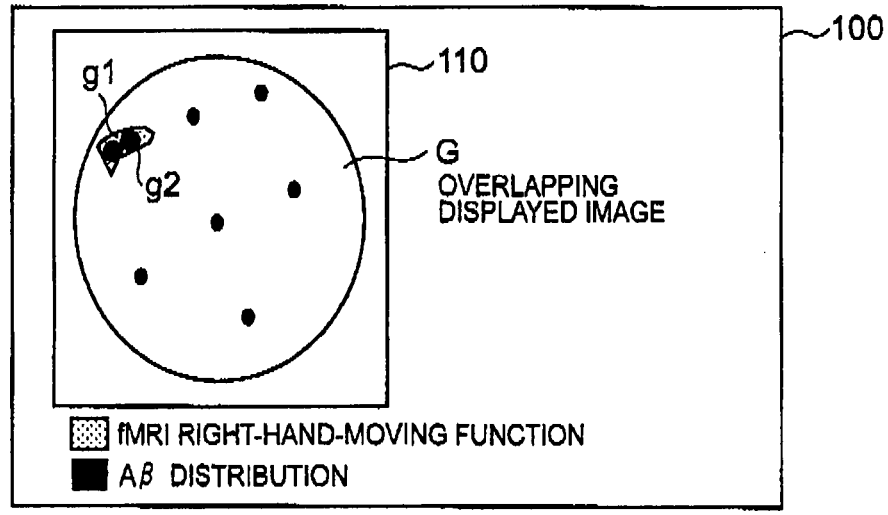

The overlapping displayed image G shown in FIG. 3(C) represents an example of images when the brain function image G1 and the substance distribution image G2 are displayed overlapping. The overlapping displayed image G is an image in which the brain function image G1 and the substance distribution image G2 are displayed overlapping by associating each of parts (coordinate) within the brain with each other. When the overlapping displayed image G is displayed, as shown in the bottom portion of the image display region 110 in the FIG. 3(C), information indicating a body part or a function "fMRI right hand action function" (including a modality name) corresponding to the active region image g1, or information indicating the distributions of a substance image g2 "Aβ distribution" is displayed.

Figure 4:
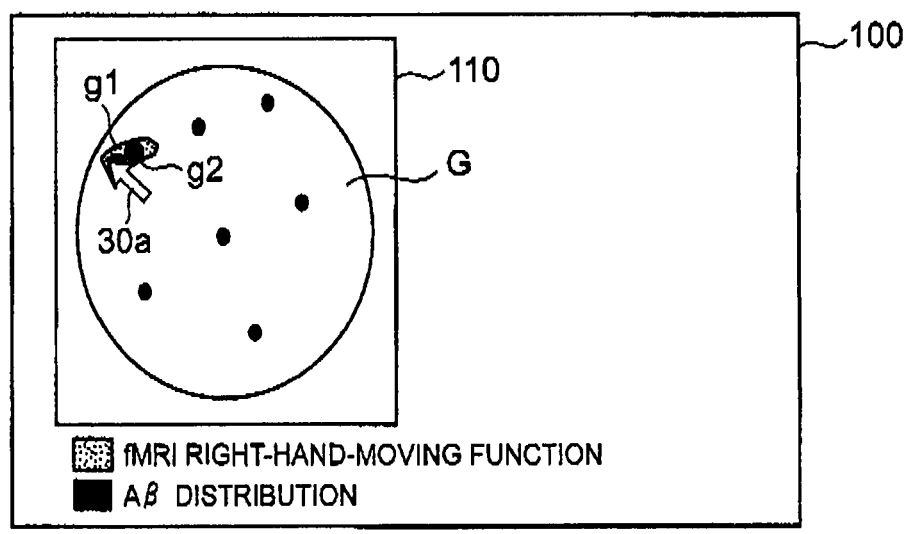
FIG. 4 is a schematic diagram showing an example of embodiments of image display of the medical diagnosis assistance system according to the present invention.

Next, when the user operates and clicks the mouse of the operation device 30 by pointing the mouse pointer 30a to the active region image g1 (or the substance image g2) as shown in FIG. 4 (S6), the system control part 11 reads out a plurality of substance distribution information 12b from the storage part 12 and sends the same to the changing information-generating part 13. The changing information-generating part 13 generates information of substance quantity changes indicating changes in quantity over time of specified endogenous substances in a part within the brain that corresponds to the clicked active region image g1, based on the plurality of substance distribution information 12b (S7).

Subsequently, the estimate calculation part 14 calculates estimates of the quantity of a specified endogenous substance in a part that corresponds to the clicked active region image g1, based on the information of substance quantity changes (S8). The obtained estimates are sent to the graph information-generating part 15 along with the information of substance quantity changes.

The graph information-generating part 15 generates image data of graph information indicating the changes in quantity over time of specified endogenous substances in a part that corresponds to the clicked active region image g1, based on the information of substance quantity changes and the estimates (S9). The image data of the graph information is sent to the display control part 19.

The display control part 19 causes the display device 20 to display the graph information indicating the changes in quantity over time of specified endogenous substances in a part that corresponds to the clicked active region image g1, based on the image data (S10). This graph information is displayed on a graph information display region 120 of the screen for medical treatment 100. Moreover, the graph information may also be displayed by pop-up in a window that displays the graph information.

Figure 5:
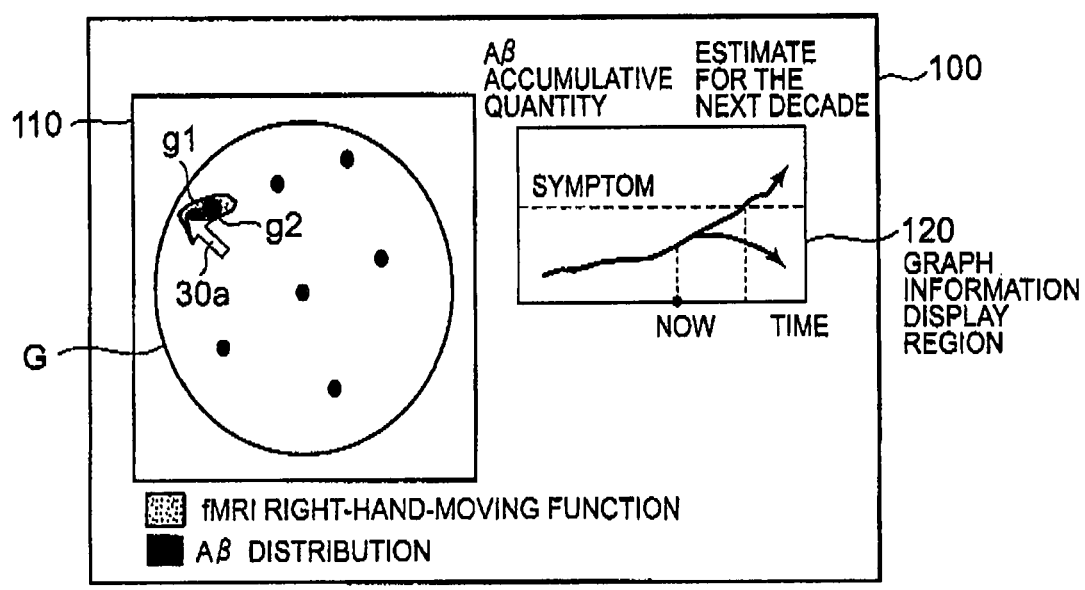
FIG. 5 is a schematic diagram showing an example of embodiments of image display of the medical diagnosis assistance system according to the present invention.

One example of display modes of the graph information is shown in FIG. 5. The graph information shown in FIG. 5 represents a graph wherein the horizontal axis represents the "Time" and the vertical axis represents the accumulative quantity (abundance) of a specified endogenous substance (Aβ). "Now" on the horizontal axis indicates the current point. In the horizontal axis, to the left of "Now" is the past, whereas the right side thereof is the future. Therefore, the portion on the left of "Now" on a graph is generated based on the information of substance quantity changes. On the other hand, the portion on the right of "Now" on a graph is generated based on the estimates. The graph information is a prediction of the changes of the accumulative quantity of the Aβ from the present to 10 years from now.

To the right of "Now," a graph line rising over time and a declining graph line are shown. The rising graph line shows estimate of changes (increase) in the accumulative quantity of Aβ when no medical treatment such as rehabilitation is performed (a graph based on the previously described information regarding estimate when not providing medical treatment). On the other hand, the declining graph line shows estimate of changes (decrease) in the accumulative quantity of Aβ when medical treatment has been performed (a graph based on the previously described information of estimate when performing).

Furthermore, the dotted line displayed in parallel to the horizontal axis in a graph information display region 120 indicates the accumulative level of the Aβ wherein symptoms of Alzheimer's disease appear.

Second Operation

Figure 6:
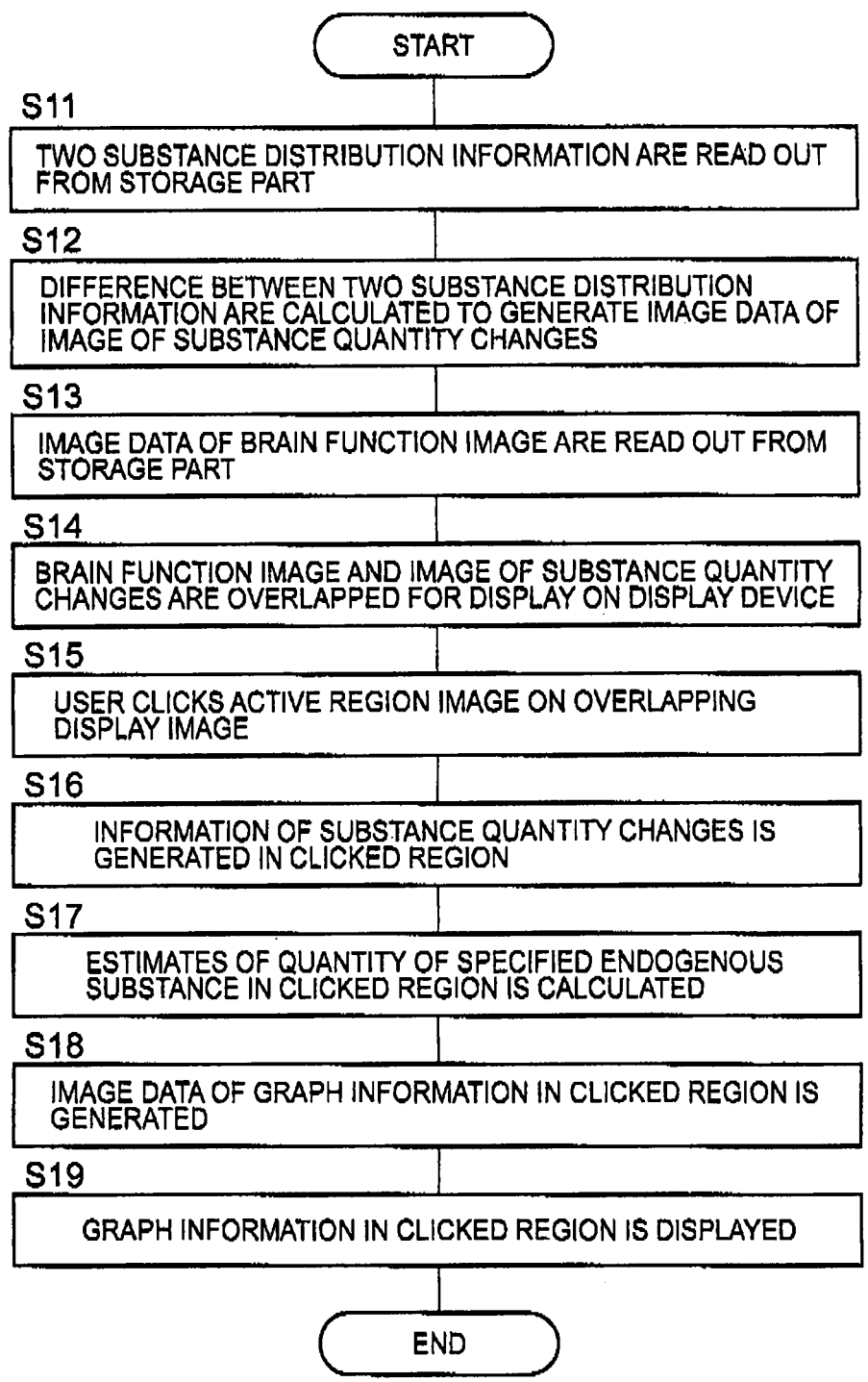
FIG. 6 is a flow chart showing an example of embodiments of operation of the medical diagnosis assistance system according to the present invention.

The flow chart shown in FIG. 6 represents one example of operations performed by the medical diagnosis assistance system 1 when a brain function image and an image of substance quantity changes are displayed in the display device 20. It should be noted that the following processes have already been performed: acquisition of the substance distribution information via the molecular imaging device 2 (S1); acquisition of the image data of the brain function image via the fMRI device 3 (S2); storage of the substance distribution information and the image data of the brain function image in the medical image database 4 (S3); and reading out of image data 12a of the brain function image and the substance distribution information 12b via the system control part 11 of the control device 10 as well as storage of the same in the storage part 12 (S4).

The system control part 11, for example, reads out two substance distribution information 12b with different examination dates/time from the storage part 12 in response to an operation by the user (an operation of designating the examination date/time of the substance distribution information for a difference calculation, or the like) (S11). The two substance distribution information 12b that have been read out are sent to the difference-calculating part 16.

The difference-calculating part 16 calculates the difference between the two substance distribution information 12b and generates image data of a differential image (image of substance quantity changes) of the two substance distribution information 12b (S12). The image data of the image of substance quantity changes is sent to the display control part 19.

Furthermore, the system control part 11, for example, reads out the image data 12a of the brain function image that has been acquired on the same examination day/time as one of the two substance distribution information 12b that have been read out in Step S11 from the storage part 12 and sends the same to the display control part 19 (S13).

The display control part 19 causes the display device 20 to display the image of substance quantity changes and the brain function image overlapping, based on the image data from the difference-calculating part 16 and the image data 12a from the system control part 11 (S14). In the accordingly displayed image, the image of substance quantity changes and the brain function image are displayed overlapping while associating each of parts (coordinate) within the brain with each other (that is, the image of substance quantity changes is displayed by replacing the substance distribution image G2 in FIG. 3). This is similar to the case of the overlapping displayed image G that is shown in FIG. 3(C).

Next, as in Step S6 of FIG. 2, when the user clicks the active region image g1 (S15), the changing information-generating part 13 generates the information of substance quantity changes in a part within the brain that corresponds to the clicked active region image g1, based on a plurality of substance distribution information 12b that is sent from the system control part 11 (S16). Subsequently, the estimate calculation part 14 calculates estimates of the quantity of a specified endogenous substance in the part based on the information of substance quantity changes (S17). Furthermore, the graph information-generating part 15 generates image data of the graph information in the part based on the information of substance quantity changes and the estimates (S18).

Based on the image data, the display control part 19 causes the display device 20 to display the graph information indicating the changes in quantity over time of specified endogenous substances in a part that corresponds to the clicked active region image g1 (S19). The graph information is displayed in the graph information display region 120 of a screen for medical treatment 100. The graph information is displayed by the same mode as in FIG. 5. Furthermore, modification may be applied appropriately, e.g., clearly displaying on the horizontal axis the examination date/time of the two substance distribution information 12b used in the process of generating the image of substance quantity changes (differential image).

Third Operation

Figure 7:
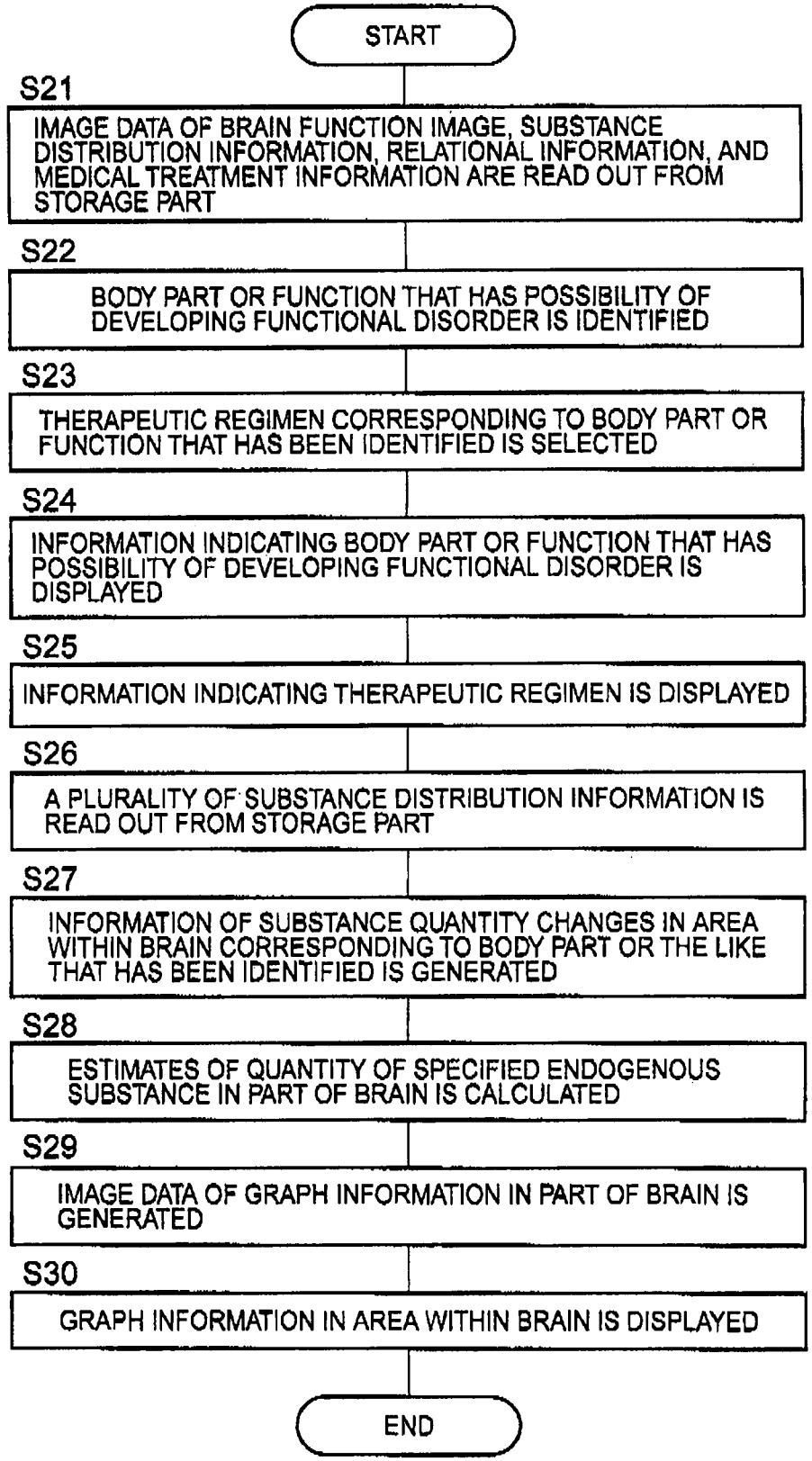
FIG. 7 is a flow chart showing an example of embodiments of operation of the medical diagnosis assistance system according to the present invention.

The flow chart shown in FIG. 7 represents one example of operations performed by the medical diagnosis assistance system 1 when a body part or a function that has the possibility of developing a functional disorder is displayed by the display device 20. It should be noted that the following process has already been performed as in the Second Operation: acquisition of the substance distribution information via the molecular imaging device 2 (S1); acquisition of the image data of the brain function image via the fMRI device 3 (S2); storage of the substance distribution information and the image data of the brain function image in the medical image database 4 (S3); and reading out of the image data 12a of the brain function image and the substance distribution information 12b via the system control part 11 of the control device 10 and storing the same in the storage part 12 (S4).

The system control part 11, for example, reads out the image data 12a of the brain function image, substance distribution information 12b, relational information 12c, and medical treatment information 12d from the storage part 12 in response to an operation by the user (S21). Herein, the image data 12a of the brain function image and the substance distribution information 12b that are read out are acquired, e.g., on the latest examination date/time. Among the data that has been read out, the image data 12a of the brain function image, substance distribution information 12b, and relational information 12c are sent to the identifying part 17.

The identifying part 17 identifies a body part or a function that has the possibility of developing a functional disorder, based on the image data 12a of the brain function image, substance distribution information 12b, and relational information 12c from the system control part 11 (S22). The information of the body part or the function that has been identified is sent to the display control part 19 Moreover, the body part or the function that has been identified is also sent to the system control part 11.

The system control part 11 selects a therapeutic regimen that matches the body part or the function that has been identified in the Step S22 from the medical treatment information 12d (S23). The information of the selected therapeutic regimen is sent to the display control part 19.

The display control part 19 causes the display device 20 to display character information or image information indicating the body part or the function that has the possibility of developing a functional disorder based on the information that has been sent from the identifying part 17 (S24). Furthermore, the display control part 19 causes the display device 20 to display the character information or the image information indicating the therapeutic regimen that matches the body part or the function based on the information that has been sent from the system control part 11 (S25). These character information or image information are displayed, for example, in a specified display region (not illustrated) of the screen for medical treatment 100.

The character information indicating the body part or the function that has a possibility of developing a functional disorder, may be displayed. The character information may be, for example, a message such as "it is expected that a functional disorder will develop on the right hand three years in the future". Furthermore, the image information indicating the body part or the function that has the possibility of developing a functional disorder may be displayed, for example, by displaying a body image in which a body is schematically represented as well as by displaying an image clearly indicating (displayed in a different color or gradation) a part of the body image equivalent to the part or the function that has the possibility of developing a functional disorder.

Furthermore, a message as the character information may be displayed indicating the therapeutic regimen with respect to the body part or the function that has the possibility of developing a functional disorder. The message is, for example, "rehabilitation for the right hand is recommended". At this moment, information may also be displayed, e.g. a practical method of medical treatment such as rehabilitation, start time, required period, and effects (promotion of the functional alternative for the brain or the like). Moreover, the image information indicating the therapeutic regimen with respect to the body part or the function that has the possibility of developing a functional disorder may be displayed, for example, an image (still image, animated image) in which the patient who is involved in the therapeutic regimen (rehabilitation), illustration, animation, and the like.

Next, for example, in response to an operation by the user through the operation device 30, the system control part 11 reads out a plurality of substance distribution information 12b from the storage part 12 and sends the same to the changing information-generating part 13 (S26). The changing information-generating part 13 generates information of substance quantity changes based on the plurality of substance distribution information 12b (S27). The information of substance quantity changes indicates changes in quantity over time of specified endogenous substances in a part within a brain corresponding to the body part or the function that has been identified in Step S24.

Subsequently, the estimate calculation part 14 calculates estimates of an abundance of a specified endogenous substance in the part within the brain, based on the information of substance quantity changes (S28). The estimates are sent to the graph information-generating part 15 along with the information of substance quantity changes.

The graph information-generating part 15 generates image data of the graph information indicating the changes in quantity over time of specified endogenous substances in the part within the brain, based on the information of substance quantity changes and the estimates (S29). The image data of the graph information is sent to the display control part 19.

The display control part 19 causes the display device 20 to display the graph information indicating the changes of the abundance of the specified endogenous substance in the part within the brain based on the image data (S30). The graph information is displayed, for example, in the graph information display region 120 of the screen for medical treatment 100. The graph information displayed here, for example, as in FIG. 5, includes: a graph showing the changing state of the accumulative quantity of a specified endogenous substance when no medical treatment such as rehabilitation was performed; and a graph showing the changing state of the accumulative quantity of the specified endogenous substance when medical treatment was performed.

Thereby, shown in the screen for medical treatment 100 are: information indicating a body part or a function that has the possibility of developing a functional disorder; information indicating the therapeutic regimen with respect to the body part or the function; a graph showing the changing state of the accumulative quantity of a specified endogenous substance when no medical treatment related to the treatment was performed; and a graph showing the changing state of the accumulative quantity of the specified endogenous substance when medical treatment was performed.

Fourth Operation

Figure 8:
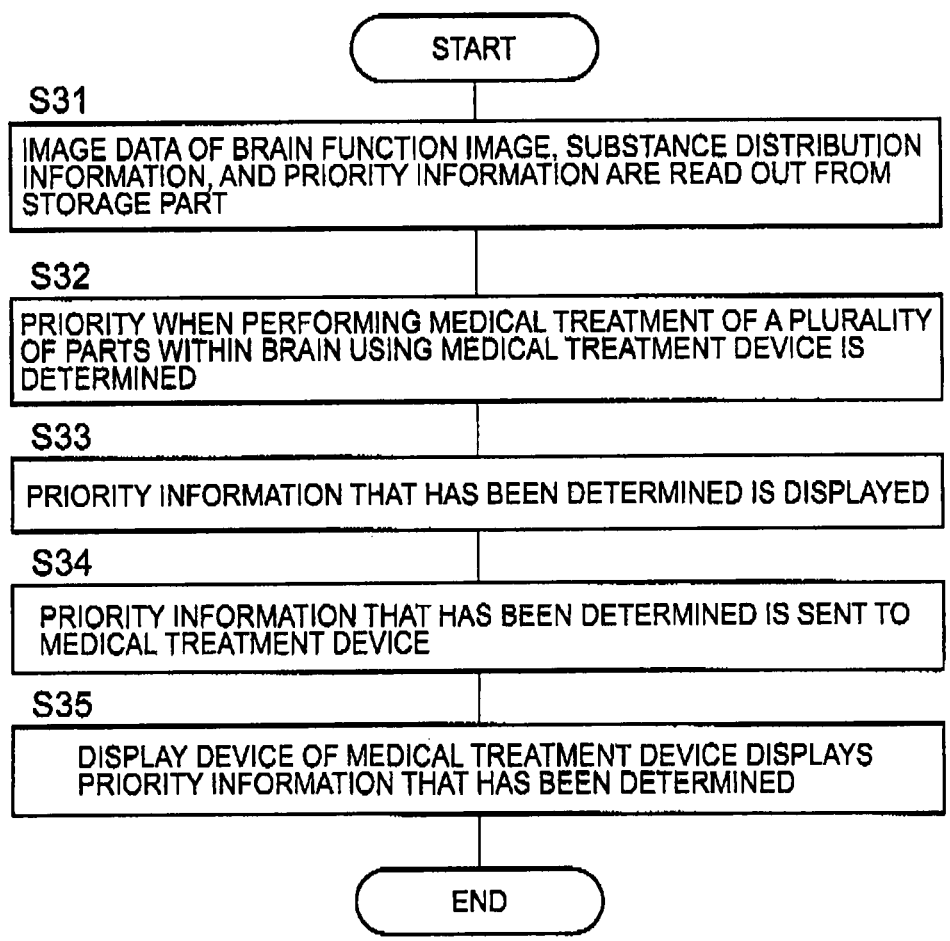
FIG. 8 is a flow chart showing an example of embodiments of operation of the medical diagnosis assistance system according to the present invention.

The flow chart shown in FIG. 8 represents one example of operations performed by the medical diagnosis assistance system 1 when the priority is displayed in the display device 20 in the event of performing medical treatment with respect to a plurality of parts within a brain using the medical treatment device 5. It should be noted that the following processes have already been performed as in the Second Operation: acquisition of the substance distribution information via the molecular imaging device 2 (S1); acquisition of the image data of the brain function image via the fMRI device 3 (S2); storage of the substance distribution information and the image data of the brain function image in the medical image database 4 (S3); and reading out of the image data 12a of the brain function image and the substance distribution information 12b via the system control part 11 of the control device 10 as well as storage of the same in the storage part 12 (S4).

The system control part 11, for example, reads out the image data 12a of the brain function image, substance distribution information 12b, and priority information 12e from the storage part 12 in response to an operation by the user (S31). Herein, the image data 12a of the brain function image and the substance distribution information 12b that are read out, for example, were acquired at the latest examination date/time. The data that has been read out is sent to the priority determining part 18.

The priority determining part 18 determines the priority when the medical treatment of a plurality of parts within a brain are performed using the medical treatment device 5, based on the image data 12a of the brain function image, substance distribution information 12b, and the priority information 12e from the system control part 11 (S32). The information indicating the priority is sent to the display control part 19.

The display control part 19 causes a display device 200 to display the priority information in the event of performing the medical treatment of the plurality of parts within the brain using the medical treatment device 5 based on the information from the priority determining part 18 (S33). As for the display mode of the information, for example, the plurality of parts within the brain may be arranged and displayed in an order corresponding to the priority. Furthermore, it is also possible to display information such as the emergency level with respect to the each of the parts (determined based on the quantity of specified endogenous substances and clinical data).

Herein, if the place where the medical treatment is performed and the place where the display device 20 is placed are different, such as in a case in which the medical treatment device 5 is placed in a room that is different from the display device 20, it is ideal to use a medical treatment device 5 equipped with a display device, or to place a display device in a location proximal to the medical treatment device 5. This display device is represented by symbol 20' (not illustrated). The medical treatment device 5 (or in the proximal location thereto) a control device (computer) is installed for displaying images or screens in the display device 20'.

In this case, the control device 10 executes the following process in addition to the above steps S31 through S33 (or in place of step S33).

The system control part 11 receives the priority information of the plurality of parts within the brain that has been determined by the priority determining part 18 in Step S32 and sends this information to the medical treatment device 5 via a network N (S34). The medical treatment device 5 causes the display device 20' to display the priority information of the plurality of parts within the brain based on the information received from the system control part 11 (S35).

Moreover, it is not necessary to display the priority information with respect to the display device 20' when the control device 10 determines the priority, but, for example, the display with respect to the display device 20' may be conducted in the following process.

First, the process up to determination of the priority (S32) is executed in advance, and the priority information is stored in the storage part 12 while linking the priority information to the patient's identification information.

When performing medical treatment via the medical treatment device 5, the user enters the patient's identification information in the medical treatment device 5 (or, in a nearby computer; referred to as the same way from hereon). The medical treatment device 5 sends the entered patient's identification information to the control device 10. The system control part 11 searches the priority information that is linked to the received patient's identification information from the storage part 12 and sends the same to the medical treatment device 5. The medical treatment device 5 then causes the display device 20' to display the received priority information.

Action, Effect

According to the medical diagnosis assistance system 1 that operates as described above, the following actions and effects are expected.

The medical diagnosis assistance system 1 operates as follows. First, the fMRI device 3 generates image data 12a of a brain function image representing the active state of a specified part within the brain of a subject. Next, the molecular imaging device 2 acquires substance distribution information 12b indicating the distribution of the quantity of a specified endogenous substance within the brain of the subject. Then, the control device 10 causes the display device 20 to display the brain function image based on the image data 12a that has been generated by the fMRI device 3 and the image information based on the substance distribution information 12b that has been acquired by the molecular imaging device 2.

According to the medical diagnosis assistance system 1 that operates as described above, functions of the central nerve or a body can be realized based on displayed brain function images. Further, substances that are present within a brain can be realized based on the image information, which is based on substance distribution information 12b. By comparing both sets of information, it becomes possible to realize the relationship between the functions of the central nerve or a body and the substances that are present within the brain.

Furthermore, according to the medical diagnosis assistance system 1, because the relationship between the functions of the central nerves or a body and the substances that are present within the brain can be realized, the timing or the order (medical treatment plan) of medical treatment can be determined by considering the level of importance of a central nerve function or a body function corresponding to each part in the brain and accumulative quantity of substances in each part. Thereby, it becomes possible to improve the effectiveness and safety of medical treatment for central nerve diseases.

Furthermore, according to the medical diagnosis assistance system 1, by examining the quantity of specified endogenous substances after the initiation of medical treatment or following the medical treatment, a decrease in the quantity can be revealed to a patient. In addition, by acquiring brain function images after the initiation of medical treatment or following the medical treatment, it is possible to reveal the result of the medical treatment to the patient, such that the brain function is recovering and that a functional alternative for the brain is in progress. Thereby, it becomes possible to conduct an appropriate follow-up related to the medical treatment effects.

In order to acquire such effects as above, the medical diagnosis assistance system 1 displays the following image information along with brain function images.

First, as described in the First Operation, the medical diagnosis assistance system 1 operates to display a substance distribution image (cf. FIG. 3(B)) showing the distribution of a quantity of a specified endogenous substance within a brain and a brain function image (cf. FIG. 3(A)) overlapping (cf. overlapping displayed image G of FIG. 3(C)).

By observing the overlapping displayed image G, the user can realize the approximate quantity of Aβ (specified endogenous substance) within each part of the brain (corresponds to a body part or a function). Further, the user can easily realize the body part or a function affected by the Aβ that has been accumulated within each part of the brain. Moreover, easy and clear informed consent can be obtained by showing the overlapping displayed image G to the patient.

Furthermore, as described in the First Operation, once a region on the overlapping displayed image G is designated by a user, the medial treatment assistance system 1 operates so as to display the graph information (image information) of the quantity of a specified endogenous substance in the part within the brain that corresponds to the region, displaying parallel to the overlapping displayed image G.

Thereby, the accumulative state of the specified endogenous substance until then can be realized for each part within the brain (and thus, per body part or per function). Furthermore, it is also possible to predict what kind of effect on the central nerves or body functions can be expected in the future when the accumulation of endogenous substances continues to progress. Thereby, it becomes possible to perform an early diagnosis of a central nerve disease or to predict the progressive state of an illness with high accuracy. Moreover, easy and clear informed consent related to the progressive state or the progress prediction of the disease can be obtained by showing the graph information to the patient.

According to the medical diagnosis assistance system 1 for conducting the First Operation, because the quantity of specified endogenous substances in a plurality of parts within a brain can be realized, optimization of the timing or the order of medical treatment can be achieved by considering the level of importance of a central nerve function or a body function that corresponds to each part within the brain and also by considering the quantity of the specified endogenous substances, etc.

Moreover, as described in the Second Operation, the medical diagnosis assistance system 1 operates so as to display an image of substance quantity changes obtained from the difference of the two substance distribution information 12b with different examination dates/time, displaying it with overlapping a brain function image.

By observing the overlapping displayed image, the user can easily realize which part of the brain (that corresponds to a body part or a function), and how much the quantity of the AP (specified endogenous substance) have changed in a specified period (interval during which the two substance distribution information 12b have been acquired). Moreover, easy and clear informed consent related to the progressive state of a disease can be obtained by showing the overlapping displayed image to the patient Furthermore, as described in the Second Operation, the medical diagnosis assistance system 1 operates so as to display the graph information (image information) of the quantity of a specified endogenous substance in a specified part within a brain, displaying parallel to the overlapping displayed image of an image of substance quantity changes and a brain function image.

Thereby, the accumulative state of the specified endogenous substance in a specified period can be realized for each part within the brain (and thus, per body part or per function). Furthermore, if the accumulation of the endogenous substance continues to progress, it is also possible to predict what kind of effect on the functions of the central nerves or a body can be expected in the future. Thereby, it becomes possible to perform an early diagnosis of a central nerve disease or to predict the progressive state of the illness with high accuracy. Moreover, easy and clear informed consent related to the progressive state or the progress prediction of the disease can be obtained by showing the graph information to the patient.

In addition, as described in the Third Operation, the medical treatment diagnosis system 1 operates so as to display a body part or a function that has the possibility of developing a functional disorder based on the image data 12a of the brain function image, substance distribution information 12b, and the related information 12c.

By referring to the information, the user can easily realize a functional disorder in a body that will possibly develop in the future due to the presence of a specified endogenous substance. Furthermore, by showing this information to the patient, easy and clear informed consent related to the functional disorder that will possibly develop in the future can be achieved.

Furthermore, according to the medical diagnosis assistance system 1, because the changes of the quantity of specified endogenous substances in a plurality of parts within a brain can be realized, an optimization of the timing or the order of medical treatment can be achieved by considering the level of importance of a central nerve function or a body function that corresponds to each part within the brain and by considering the quantity of the specified endogenous substances, etc.

Moreover, as described in the Third Operation, regarding the body part or the function that has been identified as having the possibility of developing a functional disorder, the medical diagnosis assistance system 1 operates so as to display the therapeutic regimen corresponding to the body part or the function.

Thereby, the user can easily realize the therapeutic regimen that should be performed on the patient. In addition, easy and clear informed consent related to the medical treatment policy can be obtained by showing the information to the patient.

Herein, the therapeutic regimen to be displayed particularly includes therapeutic regimen such as rehabilitation for promoting a functional alternative for the brain. Therefore, it is possible to use this display information, e.g., when telling the patient what kind of mechanism of medical treatment will improve the disease.

Furthermore, as described in the Third Operation, the medical diagnosis assistance system 1 calculates estimates of the quantity of a specified endogenous substance respectively for when the therapeutic regimen was performed and when the same was not performed, and operates so as to display the graph information based on the each of the estimates.

Thereby, the expected effect of the medical treatment can be easily realized, and also the degree of deterioration of the illness in the event of not performing the medical treatment can be easily realized. Furthermore, easy and clear informed consent related to the medical treatment effect can be obtained by showing a graph representing a case in which the medical treatment was performed and a graph representing a case in which no medical treatment was performed. Such an effect is the same as in the First Operation or in the Second Operation.

Furthermore, in this embodiment, a graph is to be displayed by calculating both estimates for when the therapeutic regimen was performed and when the same was not performed, by the constitution, but the estimate of only one of these may be calculated and displayed as a graph.

Moreover, according to the medical diagnosis assistance system 1 for conducting the Third Operation, in case when a plurality of body parts or functions are identified as having the possibility of developing a functional disorder, graph information in a part within the brain corresponding to the each part or each function that has been identified can be compared and studied. Thereby, the optimization of the timing or the order of the medical treatment can be achieved by considering the level of importance of the central nerves functions or body functions, and by considering the quantity of the specified endogenous substance etc.

Furthermore, as described in the Fourth Operation, the medical diagnosis assistance system 1 operates so as to determine and display the priority when performing a medical treatment via the medical treatment device 5 with respect to a plurality of parts within a brain based on the image data 12a of brain function images, the substance distribution information 12b, and priority information 12e.

The priority information is an objective material regarding the order of the medical treatment for the plurality of parts within a brain and is intended to contribute to the safety of the medical treatment of a central nerve disease or the improvement of the medical treatment effect. Moreover, the priority information can be used effectively as a resource for eventually determining the order of the medical treatment. Furthermore, it is also possible to use the priority information as a resource in the event of explaining the order of the medical treatment to a patient.

MODIFIED EXAMPLE

The constitution of the medical diagnosis assistance system 1 described thus far is simply a practical example of a preferable implementation of the present invention. Therefore, optional modifications can be applied as needed with respect to the constitution. Hereafter, various kinds of modified examples that are to be included in the present invention are described.

In the above embodiment, graph information is to be displayed (First Operation, Second Operation) when the user designates a region on an overlapping displayed image (cf. FIG. 3(C), etc.). However, in the medical diagnosis assistance system related to the present invention, the display timing of graph information is not limited to this.

For example, a software key or the like can be installed for designating a part within a brain (or a body part or a function). Then, it is possible to constitute it so that by responding to the operation of the software key (e.g., being clicked), information of substance quantity changes in the designated part is generated; estimates are calculated; image data of graph information is generated; and the graph information is displayed in the display device 20 (e.g., the graph information display region 120 of the screen for medical treatment 100).

Figure 9:
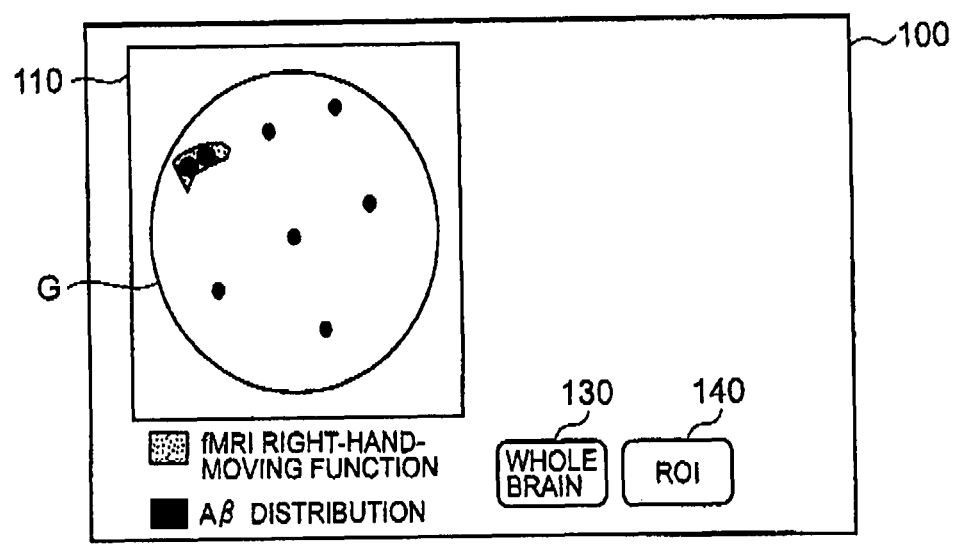
FIG. 9 is a schematic diagram showing an example of displaying embodiments by the modified example of the medical diagnosis assistance system according to the present invention.
Figure 10:
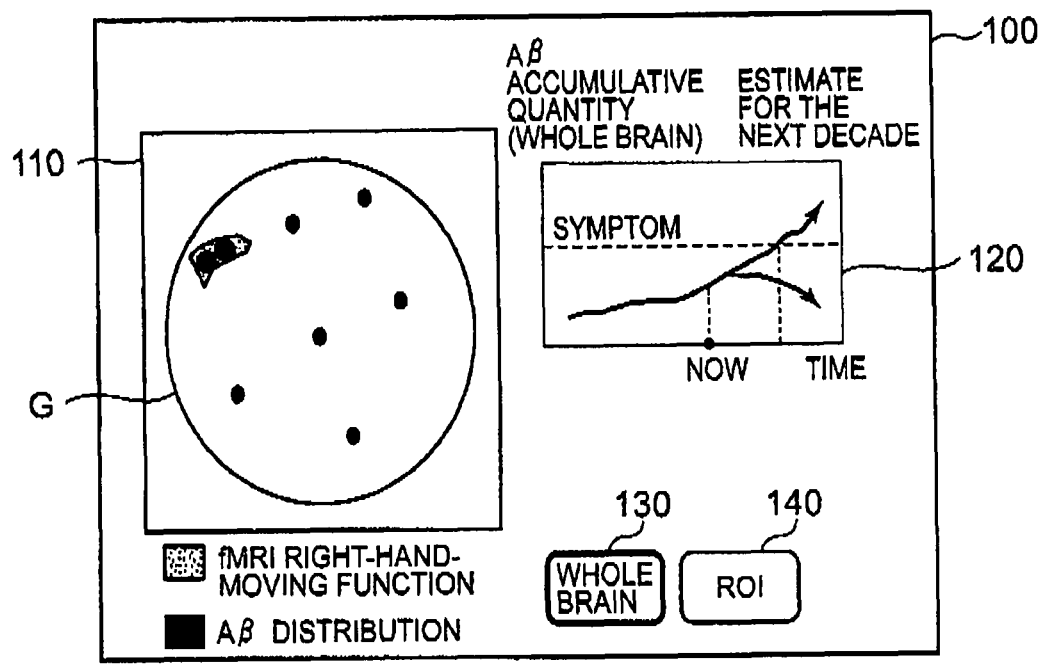
FIG. 10 is a schematic diagram showing an example of displaying embodiments by the modified example of the medical diagnosis assistance system according to the present invention.
Figure 11:
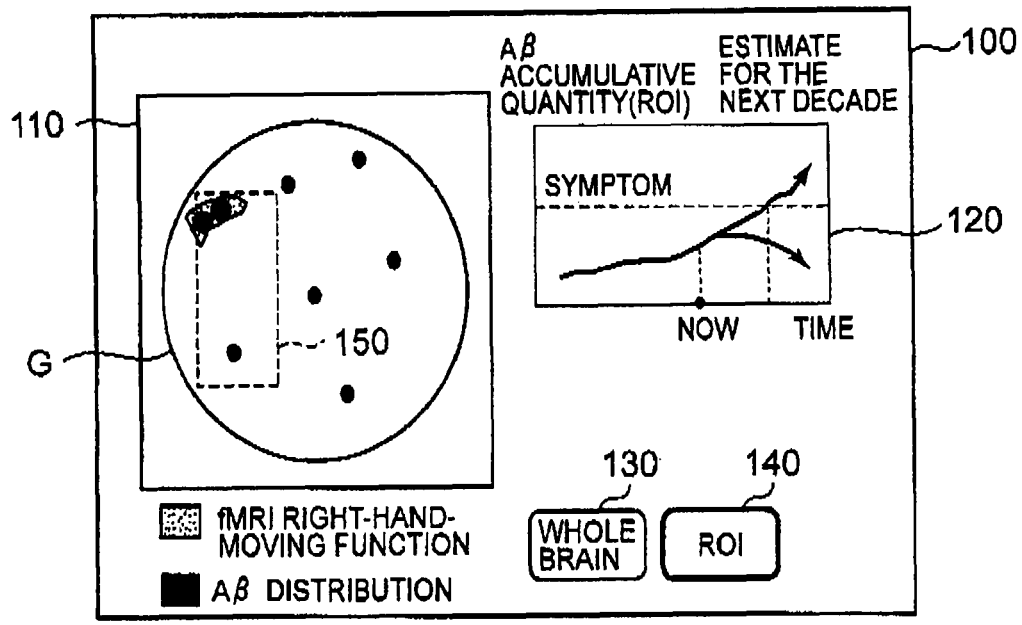
FIG. 11 is a schematic diagram showing an example of displaying embodiments by the modified example of the medical diagnosis assistance system according to the present invention.

The illustrative examples of this modification are shown in FIG. 9 to FIG. 11. In the screen for medical treatment 110 shown in FIG. 9, the whole brain button 130 and ROI (region of interest) button 140 as well as the image display region 100 similar to the abovementioned embodiments are provided. The whole brain button 130 is operated (clicked) for specifying the whole brain as an analysis target. The ROI button 140 is operated for specifying the region of interest that has been entered by a user as an analysis target.

In the image display region 110, the overlapping display image G equivalent to the whole brain is shown. Moreover, instead of the overlapping display image G, either one of the brain function image G1 or the substance distribution image G2 may be shown. The image shown in the image display region 110 may be a three-dimensional image or a tomographic image that shows the whole brain.

When the whole brain button 130 is operated, the total quantity of a specified existing endogenous substance (Aβ etc.) in the whole brain is calculated and displayed. Furthermore, as shown in FIG. 10, graph information indicating changes over time in the total quantity of a specified endogenous substance in the whole brain can also be displayed in the graph information display region 120.

As described, by displaying the total quantity in the whole brain or the graph information, the total quantity of a specified endogenous substance in the whole brain can be easily realized. Meanwhile, the changes in the total quantity over time of a specified endogenous substance in the whole brain can be understood easily.

Usage of the ROI button 140 will be described. First, a user enters the ROI into the overlapping display image G by operating the operation device 30 (e.g., mouse drag operation). Next, the user clicks the ROI button 140. This calculates and displays the total quantity of a specified existing endogenous substance in the ROI. Furthermore, as shown in FIG. 11, graph information indicating changes over time in the total quantity of a specified endogenous substance in the ROI can also be displayed in the graph information display region 120.

As described, by displaying the total quantity in the ROI or the graph information, the total quantity of a specified endogenous substance in a desired region in the brain can be easily realized. Meanwhile, the changes over time in the total quantity of a specified endogenous substance in the desired region in the brain can be easily realized.

In addition, because specifying the whole brain is synonymous with specifying the whole brain as the ROI, it is not necessary to provide a means for specifying the whole brain, such as by the whole brain button 130. When observing the whole brain at all times without specifying the ROI, it is not necessary to provide an ROI button 140.

Furthermore, it is also possible to automatically determine a part within a brain for which graph information is to be displayed. For this purpose, for example, the following constitution can be adapted. First, parts within the brain in which the active state has diminished over time are extracted based on a plurality of image data 12a of brain function images with different examination dates/time. Specifically, the parts in which the active state has diminished can be extracted by obtaining the difference of two image data 12a of the brain function images with different examination dates/time. Also, the parts in which the active state has diminished can be extracted by tracking the changes in luminance (gradation value) of each pixel of the image data 12a.

Next, in the substance distribution information 12b (image data) of the latest examination date/time, parts (pixel) within the brain in which a specified endogenous substance is present are detected.

Subsequently, the parts (pixel coordinate) within the brain that were extracted with regard to the active state thereof have diminished over time, and the detected parts (pixel coordinate) within the brain regarded to have a specified existing endogenous substance (e.g., more than a specified amount) are compared to extract parts that are mutually positioned at the same coordinate. In other words, the parts within the brain in which the active state thereof has diminished and in which a specified endogenous substance present are extracted.

Among the parts that have been extracted, for example, a part with a maximum quantity of a specified substance is determined as a part for which graph information is to be displayed. Furthermore, weighting in accordance with the function is applied for each part within a brain, and a part for which graph information is to be displayed can also be determined based on the weight and the quantity of a specified endogenous substance.

In the above embodiment, the estimate calculation part 14 for calculating estimates of a quantity of a specified endogenous substance is provided. However, in the present invention, it is also possible to adopt a constitution that does not provide the estimate calculation part 14. In this case, graph information indicating changes in the quantity of a specified endogenous substance up to the latest examination date/time is displayed.

In the above embodiment, the case was described in which a subject to be detected by the molecular imaging device 2 is Aβ, but, for example, the quantity of active oxygen or the quantity of cells that have died by apoptosis can be the target to be detected by the molecular imaging device 2. In the case of detecting active oxygen, for example, medical drugs disclosed in International Patent Publication No. WO99/59642 can be adapted. Furthermore, in the case of detecting cells that have died by apoptosis as a target, for example, methods disclosed in Published Japanese Patent Translation of PCT No. 2005-523945, Published Japanese Patent Translation of PCT No. 2004-535375, and Published Japanese Patent Translation of PCT No. 2004-529922, etc., can be employed.

In the above embodiment, parts within a brain and body parts or functions have been associated, but the part can be associated with other parts connected through nerve bundles with respect to the part in which a specified endogenous substance is present, by detecting the morphology of nerve bundles in the brain. Thereby, the development of a functional disorder of a body part corresponding to the other parts that have no direct relationship with the part in which a specified endogenous substance is present can be realized. Furthermore, as a method of detecting the morphology of nerve bundles in a brain, for example, a method of fiber tracking via an MRI device can be employed (e.g., cf. Web page http://www.shouwa.or.jp/tomo/ota02_05/tomo/iryo/gaku2.htm, or Published Japanese Patent Translation of PCT No. 2003-528676).

In the above embodiment, a medical imaging diagnosis apparatus such as a fMRI device 3 is used for actually generating the image data of the brain function image, however this invention is not limited to this embodiment. For example, in the research of prior art, a standard distribution of functions within a brain is already known. This type of distribution is referred to as a brain map. As a specific example of this brain map, the brain map of Brodmann and the brain map of Penfield are known.

In this modified embodiment, instead of the image data actually obtained by the medical imaging diagnosis device, the image data of the brain map is stored in advance in an arbitrary medical data storing part (e.g. the storing part 12 or the medical image database 4). Then, this brain map is displayed together with the substance distribution image G2. The displaying mode may be similar to the overlapping displaying mode in the above embodiment, or other mode may be also applicable.

As described above, by displaying the brain map as the brain function image, even if the brain function image of the subject is not actually obtained, both the function of the central nerve or the body and the substance within the brain can be realized. Further, by comparing both, the relation between the function of the central nerve or the body and the substance within the brain can be realized.

On the other hand, because the standard brain map is used in the above modified example, the accuracy of diagnosis is inevitably less than the one used in the above embodiment. For example, when a functional alternative for the brain occurs, the state within the brain of the subject is difficult to be accurately realized. However, though roughly depicted, it is advantageous that both the function of the central nerve or the body and the state of the substance within the brain can be relatively easily realized. Particularly, it is advantageous to be applicable to the medical institution without an fMRI device.

When taking the disadvantage of the above modified embodiment into account, the following modified example is also applicable. In this modified example, the image data of the brain function image of the subject is actually obtained at least once. Then, the image data of this brain function image is stored, and this brain function image is read out and displayed together with newly obtained substance distribution image. Further, based on the image data of this brain function image, the image data of a function distribution image within the brain of the subject (an image similar to the standard brain map) may be generated.

This processing is performed based on the image data of the actually generated brain function image, for example, by associating the part in the brain with the body function (or the body part) and imaging the result. This processing is performed by the microprocessor of the control device 10 (function distribution generating part). The function distribution image, for example, represents the distribution of the body function within the brain by using the displaying color and character string information.

According to this modified example, the function distribution within the brain of the subject is understood. Therefore, the accuracy of the diagnosis is expected to improve compared to the case using the standard brain map.

On the other hand, when a symptom of functional alternative for the brain appears, it is desirable to actually obtain the image data of new brain function image and to display this new brain function image together with the new substance distribution image. By appropriately renewing the brain function image as described above, it is possible to process in response to the change of function distribution within the brain of the subject.

Instead of displaying the brain function image and the substance distribution image as the above embodiment (or together with displaying them), the brain function image and the substance distribution image may be output in an arbitrary method. For example, the brain function image and the substance distribution image may be printed out on a recording paper. Alternatively, the image data may be stored in the recording medium or sent out to an external device.

The medical care assistance device according to the present invention is constituted to include, for example, the control device 10 (control part) and the display device 20 (display apparatus) shown in FIG. 1. In FIG. 1, the storage part (storage part 12) is provided within the control device 10 (control part), but it is possible to provide a storage part generally within the control part or at an optional external location.

In the above embodiment, the medical care assistance program P is stored on the hard drive of the control device 10. Alternatively, the medical care assistance program P can be stored on optional storage media that a computer can read. Storage media such as an optical disk, magneto optical disk (CD-ROM, DVD-RAM, DVD-ROM, MO, etc.), and magnetic medium (hard disk, floppy® disk, ZIP drive, etc.) can be cited as typical examples.

What is claimed is:

1. A medical diagnosis assistance system, comprising:
    an image data memory configured to store image data of a brain function image;
    a substance distribution information acquiring device configured to detect a signal from within a brain of a subject and to acquire, based on the detected signal, substance distribution information indicating distribution of a quantity of beta-amyloid in each part of the brain;
    a computer interface;
    a display; and
    a controller including a processor configured to control said display to display the brain function image and image information based on said acquired substance distribution information, wherein
    the controller is further configured to generate changing information based on a plurality of said substance distribution information acquired at a plurality of times, the changing information indicating a change in quantity over time of the beta-amyloid;
    said controller is configured to control said display to generate a superimposed image by superimposing said brain function image and a substance distribution image, with the parts in the brain corresponding to and overlapping each other, the substance distribution image indicating the distribution of the quantity of said beta-amyloid in the brain, the substance distribution image being generated from the acquired substance distribution information;
    the controller is configured to control the display to display, in response to selection of a region of the superimposed image by a user via the computer interface, graph information, with the superimposed image being displayed in parallel, the graph information being generated from the generated changing information for the region of the brain selected by the computer interface and indicating the change in the quantity over time of the beta-amyloid in the selected region of the brain;
    said controller is further configured to calculate estimates of said change in the quantity over time of said beta-amyloid based on the generated changing information; and
    said controller is configured to control said display to display said graph information reflecting said calculated estimates and said superimposed image in parallel.

2. The medical diagnosis assistance system according to claim 1, further comprising:
    a brain function image-generating device configured to detect the signal from within the brain of the subject and to generate image data indicating an active state of a part of the brain based on the detected signal,
    wherein the image data memory is configured to store the generated image data as the image data of the brain function image.

3. The medical diagnosis assistance system according to claim 1, further comprising:
    a brain function image-generating device configured to detect the signal from within the brain of the subject and to generate image data indicating an active state of a part of the brain based on the detected signal, wherein
    the controller is further configured to generate image data indicating a function distribution within the brain of the subject,
    wherein the image data memory is configured to store the generated image data as the image data of the brain function image.

4. The medical diagnosis assistance system according to claim 1, wherein the image data memory is configured to store the image data of a brain map in advance indicating a standard function distribution within the brain as the image data of the brain function image.

5. The medical diagnosis assistance system according to claim 1, further comprising:
    a memory configured to store relational information in advance that relates a part within the brain to a body part or a function controlled by the part within the brain, wherein
    the controller is further configured to identify a body part or a function that has the possibility of developing a functional disorder based on image data of the brain function image stored in said image data memory, substance distribution information acquired by said substance distribution information-acquiring device, and said stored relational information; and
    said controller is configured to control said display to display said specified body part or function.

6. The medical diagnosis assistance system according to claim 5, wherein:
    said memory is configured to store medical treatment information in advance, including therapeutic regimen for disorders of the body part or the function for each body part or function related to parts within the brain by said relational information; and
    said controller is configured to control said display to display said therapeutic regimen corresponding to the specified body part or function identified by said identifying part based on said medical treatment information.

7. The medical diagnosis assistance system according to claim 6, wherein
    said controller is further configured to:
    generate changing information based on a plurality of said substance distribution information acquired at a plurality of times by said substance distribution information-acquiring device, the changing information indicating the change in the quantity over time of said beta-amyloid; and
    calculate at least one of estimates of said change in quantity over time of said beta-amyloid in the case of said therapeutic regimen being applied indicated in said medical treatment information and estimates of said change in the quantity over time of said beta-amyloid in the case of not being applied based on said generated changing information and said stored medical treatment information; and
    said controller is further configured to control said display to display the graph information indicating said change in the quantity over time of said beta-amyloid based on the generated changing information and said calculated estimates.

8. The medical diagnosis assistance system according to claim 6, wherein:
    said therapeutic regimen of medical treatment information includes therapeutic regimen for promoting a functional alternative for the brain of said subject.

9. The medical diagnosis assistance system according to claim 7, wherein:
    said therapeutic regimen of medical treatment information includes therapeutic regimen for promoting a functional alternative for the brain of said subject.

10. The medical diagnosis assistance system according to claim 1, further comprising:
    a memory configured to store priority information in advance associating a priority of a medical treatment with each of brain parts, based on a body part or a function controlled by said brain parts, wherein said controller is further configured to determine the priority of the medical treatment for a plurality of parts within the brain based on the brain function image data stored in said image data memory, the acquired substance distribution information, and said stored priority information; and said controller is further configured to control said display to display said determined priority of parts within the brain.

11. The medical diagnosis assistance system according to claim 10, further comprising:
a medical treatment device configured to eliminate or detoxify said beta-amyloid by irradiating said beta-amyloid with energy waves.

12. The medical diagnosis assistance system according to claim 10, further comprising:
a medical treatment device configured to deliver medicine for eliminating or detoxifying said beta-amyloid toward said beta-amyloid within the brain.

13. The medical diagnosis assistance system according to claim 2, wherein:
said brain function image-generating device is configured to include an fMRI device for generating image data of said brain function image based on a blood circulation state associated with nervous activity within the brain of the subject.

14. The medical diagnosis assistance system according to claim 3, wherein:
said brain function image-generating device is configured to include an fMRI device for generating image data of said brain function image based on a blood circulation state associated with nervous activity within the brain of the subject.

15. The medical diagnosis assistance system according to claim 1, wherein:
said substance distribution information acquiring device is configured to include a molecular-imaging device to acquire, as said substance distribution information, image data indicating the distribution of the quantity of said beta-amyloid within the brain of the subject who is administered a ligand that accumulates in said beta-amyloid and a contrast agent.

16. A medical care assistance device, comprising:
a memory configured to store substance distribution information indicating a distribution of a quantity of beta-amyloid in each part of a brain of a subject and image data of a brain function image;
a computer interface;
a display; and
a controller including a processor configured to control said display to display image information based on said substance distribution information and the brain function image based on said stored image data, wherein the controller is configured to generate changing information based on a plurality of said substance distribution information acquired at a plurality of times, the changing information indicating a change in quantity over time of the beta-amyloid;

the controller is configured to control the display to generate a superimposed image by superimposing the brain function image and a substance distribution image, with the parts in the brain corresponding to and overlapping each other, the substance distribution image indicating the distribution of the quantity of the beta-amyloid in the brain, the substance distribution image being generated from the substance distribution information;

the controller is configured to control the display to display, in response to selection of a region of the superimposed image by a user via the computer interface, graph information, with said superimposed image being displayed in parallel, the graph information being generated from said generated changing information for the region of the brain selected by the computer interface and indicating the change in the quantity over time of the beta-amyloid in the selected region of the brain;

said controller is further configured to calculate estimates of said change in the quantity over time of said beta-amyloid based on the generated changing information; and said controller is configured to control said display to display said graph information reflecting said calculated estimates and said superimposed image in parallel.

* * * * *